(12) United States Patent
Gafni et al.

(10) Patent No.: US 11,761,036 B2
(45) Date of Patent: *Sep. 19, 2023

(54) METHODS, SYSTEMS AND PROCESSES OF IDENTIFYING GENETIC VARIATIONS

(71) Applicant: INVITAE CORPORATION, San Francisco, CA (US)

(72) Inventors: Erik Gafni, San Francisco, CA (US); Swaroop Aradhya, San Francisco, CA (US); Leah Matzat, San Francisco, CA (US); Eric Olivares, San Francisco, CA (US); Vinayak Kulkarni, San Francisco, CA (US); Joshua Paul, San Francisco, CA (US)

(73) Assignee: INVITAE CORPORATION, San Francisco, CA (US)

(*) Notice: Subject to any disclaimer, the term of this patent is extended or adjusted under 35 U.S.C. 154(b) by 337 days.

This patent is subject to a terminal disclaimer.

(21) Appl. No.: 17/215,433

(22) Filed: Mar. 29, 2021

(65) Prior Publication Data

US 2021/0230685 A1    Jul. 29, 2021

Related U.S. Application Data

(63) Continuation of application No. 15/711,760, filed on Sep. 21, 2017, now Pat. No. 10,995,370.

(60) Provisional application No. 62/398,268, filed on Sep. 22, 2016.

(51) Int. Cl.
*G01N 33/48* (2006.01)
*G01N 33/50* (2006.01)
*C12Q 1/6869* (2018.01)

(52) U.S. Cl.
CPC .................. *C12Q 1/6869* (2013.01)

(58) Field of Classification Search
CPC .................................... C12Q 1/6869
See application file for complete search history.

(56) References Cited

U.S. PATENT DOCUMENTS 6,534,293 B1    3/2003  Barany et al.
10,995,370 B2 *  5/2021  Gafni ............... C12Q 1/6869

FOREIGN PATENT DOCUMENTS

WO    2016/055971 A2    4/2016

OTHER PUBLICATIONS

Shpaer, EG, "GeneAssist. Smith-Waterman and other database similiarity searches and identification of motifs", Methods Mol Biol 1997, pp. 173-187, vol. 70.
Langmead, B., et al., "Ultrafast and memory-efficient alignment short DNA sequences to the human genome", Genome Biology 2009, 10:R25; available at: https://doi.org/10.1186/GB-2009-10-3-r25.
Auton, A. et al., 1000 Genomes Project Consortium, "A global reference for human genetic variation", Nature, vol. 526, Oct. 1, 2015, pp. 68-74 (available at: https://www.ncbi.nlm.gov/pubmed/26432245).

(Continued)

*Primary Examiner* — Russell S Negin
(74) *Attorney, Agent, or Firm* — PILLSBURY WINTHROP SHAW PITTMAN, LLP

(57) ABSTRACT

Provided herein are novel methods, systems and processes for generating and analyzing sequence data for the determination of the presence or absence of one or more genetic variations within a genome of a subject.

20 Claims, 13 Drawing Sheets

(56) References Cited

OTHER PUBLICATIONS

Li, H, et al., "Fast and Accurate Short Read Alignment with Burrows-Wheeler Transform", Bioinformatics, Mar. 1, 2010, pp. 1754-1760, vol. 26(5).
Li, R., et al., "SOAP2: an improved ultrafast tool for short read alignment", Bioinformatics, 2009, pp. 1966-1967, vol. 25(15).
Homer, N., et al., "BFAST: an Alignment Tool for Large Scale Genome Resequencing", PloS One, Nov. 2009, pp. 1-12, vol. 4(11).
Rizk, G., et al., "GASSST: global alignment short sequence search tool", Bioinformatics, 2010, pp. 2534-2540, vol. 26 (20).
Rivals, E., et al., "MPSCAN: Fast Localisation of Multiple Reads in Genomes", S.L. Salzberg and T. Warnos, Eds., WABI 2009, pp. 246-260, LNBI 5724.
Stranger, B., et al., "Genome-Wide Associations of Gene Expression Variation in Humans", PLoS Genetics, Dec. 16, 2005, pp. 0695-0704, vol. 1(6).
McCallum, K., et al., "Quantifying copy number variations using a hidden Markov model with inhomogeneous emission distributions", Biostatistics, Feb. 2013, pp. 600-611, vol. 14(3).
Patent Cooperation Treaty, International Search Report and Written Opinion issued in PCT/US2017/52771, dated Dec. 8, 2017, pp. 1-12.

\* cited by examiner

Fig. 11

$gt \in \{HOM\_REF, HET, HOM\_ALT\}$
$aoh \in \{True, False\}$
$R_{ij} = Read_j$ at $Site_i$
$af = 1kg\ allele\ freq$
$b = base \in \{REF, ALT, OTHER\}$ $$emission\ probability =$$

$$P(R|aoh) = \sum_{gt} \left\{ \prod_{j=1}^{R} P(b|gt) \right\} P(gt|af, aoh)$$

$$\prod_{j=1}^{R} P(b|gt)$$
$= binom(n, k, p)$
$= binom(\#\_ref, depth, p(ref|gt))$ $P(gt|af, aoh = True) = $    HWE
$P(gt = HOM\_REF) = $    $p^2$
$P(gt = HET) = $    $2pq$
$P(gt = HOM\_ALT) = $    $q^2$ $P(gt|af, aoh = False) =$
$P(gt = HOM\_REF) = $    $1 - af - .001$
$P(gt = HET) = $    $af - .001$
$P(gt = HOM\_ALT) = $    $.002$

METHODS, SYSTEMS AND PROCESSES OF IDENTIFYING GENETIC VARIATIONS

CROSS-REFERENCE TO RELATED APPLICATIONS

This patent application is a continuation of U.S. patent application Ser. No. 15/711,760, filed Sep. 20, 2017, entitled "METHODS, SYSTEMS AND PROCESSES OF IDENTIFYING GENETIC VARIATIONS", naming Erik GAFNI, Swaroop ARADHYA, Leah MATZAT, Eric OLIVARES, Vinayak KULKARNI and Joshua PAUL as inventors, and designated by attorney docket no. 055911-0454598, which claims the benefit of U.S. Provisional Patent Application No. 62/398,268 filed on Sep. 22, 2016, entitled "METHODS, SYSTEMS AND PROCESSES OF IDENTIFYING GENETIC VARIATIONS", naming Erik GAFNI, Swaroop ARADHYA, Leah MATZAT, Eric OLIVARES, Vinayak KULKARNI and Joshua PAUL as inventors, and designated by attorney docket no. 055911-0445313. The entire content of the foregoing patent applications are incorporated herein by reference, including all text, tables and drawings.

FIELD

The technology relates in part to methods, processes and systems for determination of the presence or absence of copy number variation and/or absence of heterozygosity within a genome.

BACKGROUND

Genetic information of living organisms (e.g., animals, plants, microorganisms, viruses) is encoded in deoxyribonucleic acid (DNA) or ribonucleic acid (RNA). Genetic information is a succession of nucleotides or modified nucleotides representing the primary structure of nucleic acids. The nucleic acid content (e.g., DNA) of an organism is often referred to as a genome. In most humans, the complete genome typically contains about 30,000 genes located on twenty-three pairs of chromosomes. Most genes encode a specific protein, which after expression via transcription and translation fulfills one or more biochemical functions within a living cell.

Many medical conditions are caused by one or more genetic variations within a genome. Some genetic variations may predispose an individual to, or cause, any of a number of diseases such as, for example, diabetes, arteriosclerosis, obesity, various autoimmune diseases and cancer (e.g., colorectal, breast, ovarian, lung). Such genetic variations can take the form of an addition, substitution, insertion or deletion of one or more nucleotides within a genome.

Nucleic acids of a genome can be sequenced by various methods including, for example, methods that involve massively parallel sequencing. Massively parallel sequencing (MPS) techniques often generate millions or even billions of small sequencing reads. To determine genomic sequences, each read is often mapped to a reference genome and collections of reads are assembled into a sequence representation of an individual's genome. The process of mapping and assembly of reads is carried out by one or more computers (e.g., microprocessors and memory) and is driven by a set of instructions (e.g., software instructions, code and/or algorithms).

Methods, systems and processes herein offer significant advances and improvements to current nucleic acid sequencing and analysis techniques.

SUMMARY

Presented herein, in some aspects, is a method of genome analysis that comprises (a) generating single-end sequence reads obtained from an entire genome of a subject, where (i) the reads represent less than 5% of the entire genome, (ii) the average distance between the reads is at least 4000 bp, (iii) the reads comprise sequence information for greater than 400,000 common polymorphisms, and (iv) each read comprises the sequence information for at least one of the common polymorphisms, (b) determining a presence or absence of heterozygosity for each of the common polymorphisms according to the sequence information; and (c) determining the presence or absence of a copy number variation (CNV) for a portion of the genome according to the presence or absence of heterozygosity determined in (b). In certain embodiments the presence or absence of a copy number variation is determined by a process comprising a Hidden Markov Model or Viterbi algorithm statistical model. In certain embodiments the presence or absence of a copy number variation is determined by a process comprising maximum likelihood regression, a negative binomial statistical model of the read-counts, or Expectation-Maximization. In some embodiments the method further comprises, prior to (b), determining an allele balance for one or more of the greater than 400,000 common polymorphisms, and the presence or absence of heterozygosity is determined according to the allele balances. In certain aspects, the presence or absence of a copy number variation (CNV) for a portion of the genome is determined according to the presence or absence of heterozygosity determined for a segment or contiguous portion of the genome. For example, an absence of heterozygosity as determined for a plurality of polymorphisms within a contiguous portion of the genome often indicates the presence of a CNV.

In some aspects, presented herein is a computer implemented process for performing a genome analysis where the process comprises (a) obtaining non-overlapping, single-end sequence reads obtained from an entire genome of a subject, where (i) the reads represent less than 5% of the entire genome, (ii) the average distance between reads is at least 4000 bp, and (iii) the reads comprise sequence information for greater than 400,000 common polymorphisms, and each read comprises the sequence information for at least one of the common polymorphisms, (b) determining a presence or absence of heterozygosity for each of the common polymorphisms according to the sequence information; and (c) determining the presence or absence of a copy number variation (CNV) for a portion of the genome according to the presence or absence of heterozygosity determined in (b). In some embodiments the presence of absence of heterozygosity is determined according to a plurality of allele balances determined for each of the 400,000 common polymorphisms.

In some aspects, presented herein is a non-transitory computer-readable storage medium comprising an executable program stored thereon, where the program instructs a microprocessor to (a) determine a presence or absence of heterozygosity (AOH) for plurality of common polymorphisms of a genome of a subject according to sequence information obtained from single-end sequence reads obtained from an entire genome of the subject, where (i) the reads represent less than 5% of the entire genome, (ii) the average distance between any two reads is at least 4000 bp, (iii) the reads comprise sequence information for greater than 400,000 common polymorphisms, and (iv) each read comprises sequence information for at least one of the greater than 400,000 common polymorphisms; and (b) determine the presence or absence of a copy number variation for a portion of the genome according to the presence or absence of heterozygosity determined in (a). In some embodiments the presence of absence of heterozygosity is determined according to a plurality of allele balances determined for each of the 400,000 common polymorphisms.

Certain embodiments are described further in the following description, examples, claims and drawings.

BRIEF DESCRIPTION OF THE DRAWINGS

The drawings illustrate embodiments of the technology and are not limiting. For clarity and ease of illustration, the drawings are not made to scale and, in some instances, various aspects may be shown exaggerated or enlarged to facilitate an understanding of particular embodiments.

FIG. 11 shows a process for determining an absence of heterozygosity (AOH) for a portion of a genome where R is defined as the reads for a given set of genomic sites, gt is defined as a genotype (homozygous reference, heterozygous, or homozygous alternate), aoh is a state of absence of heterozygosity or normalcy, R are the reads aligned to a particular site, af is a population allele frequency, and b represents the base or sequence at a particular polymorphic site.

DETAILED DESCRIPTION

Figure 1:
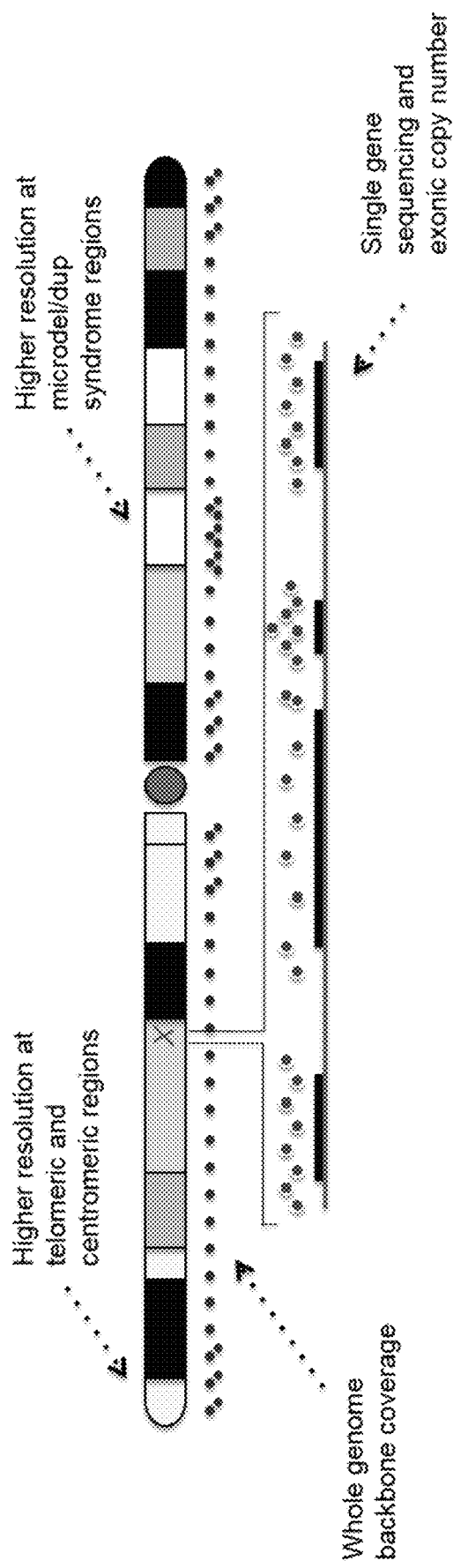
FIG. 1 shows a graphical representation of a chromosome and hypothetical optimal loci (small filled circles) identified by a target-site scoring process. Optimum loci often comprise a loci of a common polymorphism, adjacent sequence information and a primer binding site located 5' of a common polymorphism. In certain embodiments a target scoring process generates a target site score for use in selecting optimal loci for sequence read generation. In certain embodiments the target scoring process identifies optimal loci for primer binding and read generation according to loci that include a known common polymorphism, surrounding GC content, melting temperature (Tm), and distance between target-sites. The target-site scoring process often results in exclusion of problematic sites with the genome. Distance between optimal target-sites can be decreased for regions that require higher resolution, for example sites that have high clinical significance, or sites that are subtelomeric, pericentromeric, and microdel/dup syndrome regions (e.g., see lower cut out representing region X of the illustrated chromosome where the density of target sites is increased).
Figure 2:
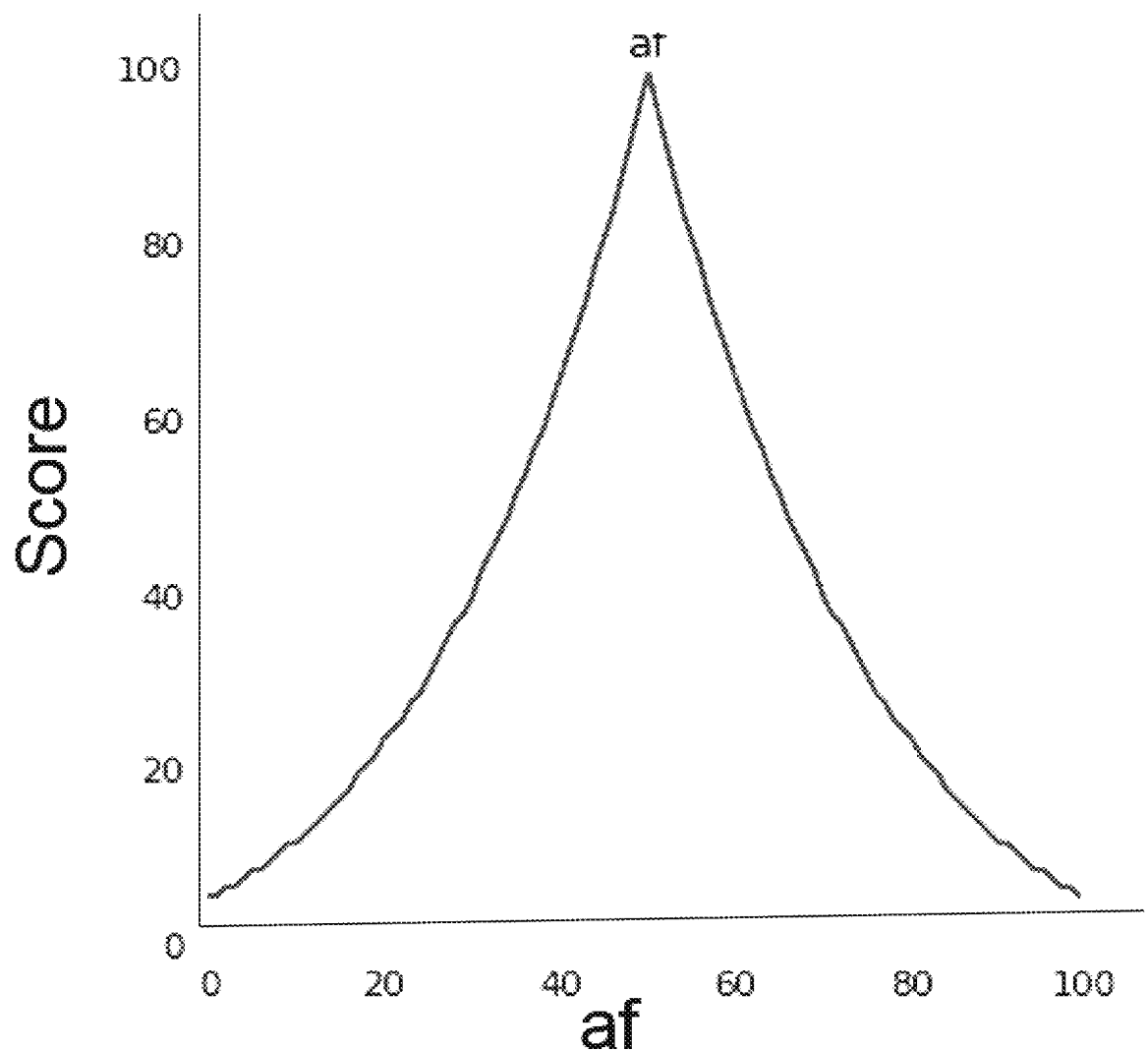
FIG. 2 shows an example of determining an allele frequency for a polymorphism at site i within a genome by use of a distribution function (e.g., $100 \times (1-|\alpha_i-0.51|)^4$ where $\alpha_i=1000$ Genomes Allele Frequency at site i).
Figure 3:
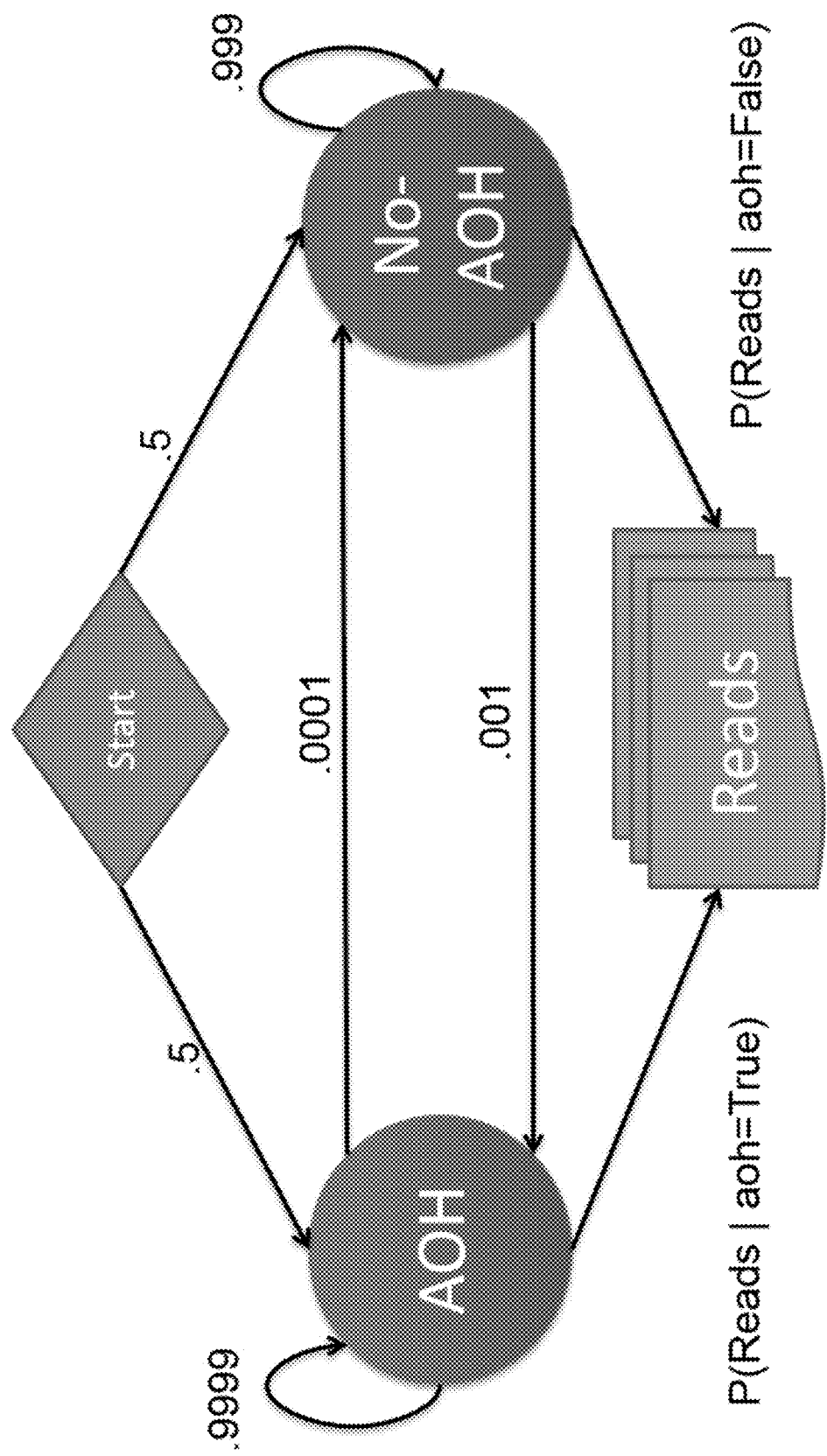
FIG. 3 shows an embodiment of a simplified version of the HMM used to model and detect AOH in which there are only states, AOH and no-AOH (normal).
Figure 4A:
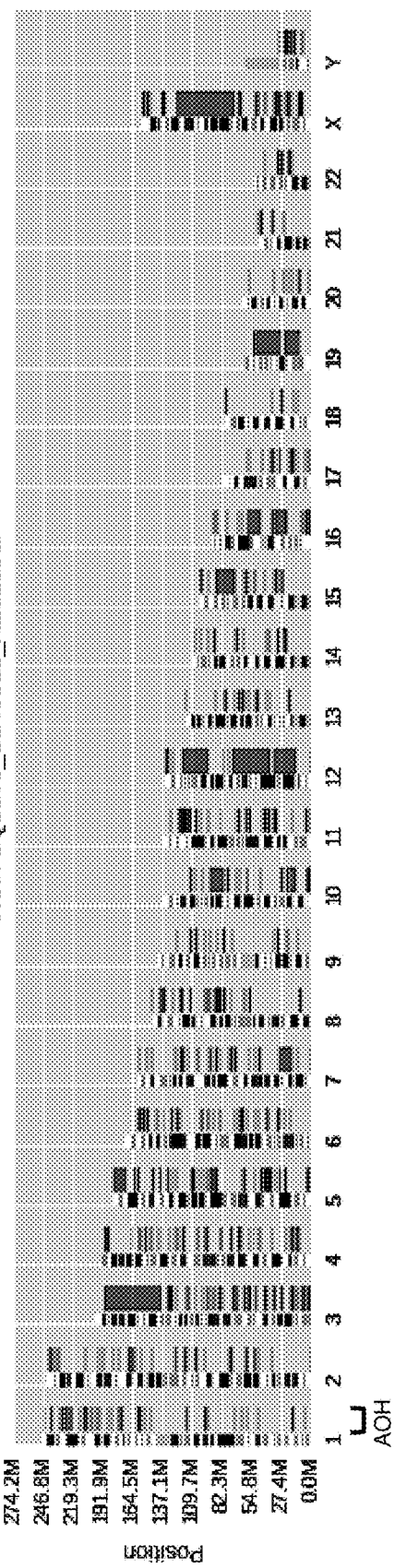
FIG. 4A-D shows a graphical illustration of AOH calls for loci of a subject's genome determined by a method described herein. Chromosome numbers are indicated on the x-axis and chromosomal positions are indicated on the Y-axis. AOH calls are indicated by dark shaded horizontal lines or bars in the column to the right of each chromosome, thereby indicating the chromosomal position of the common polymorphism from which the AOH call was derived.
Figure 4B:
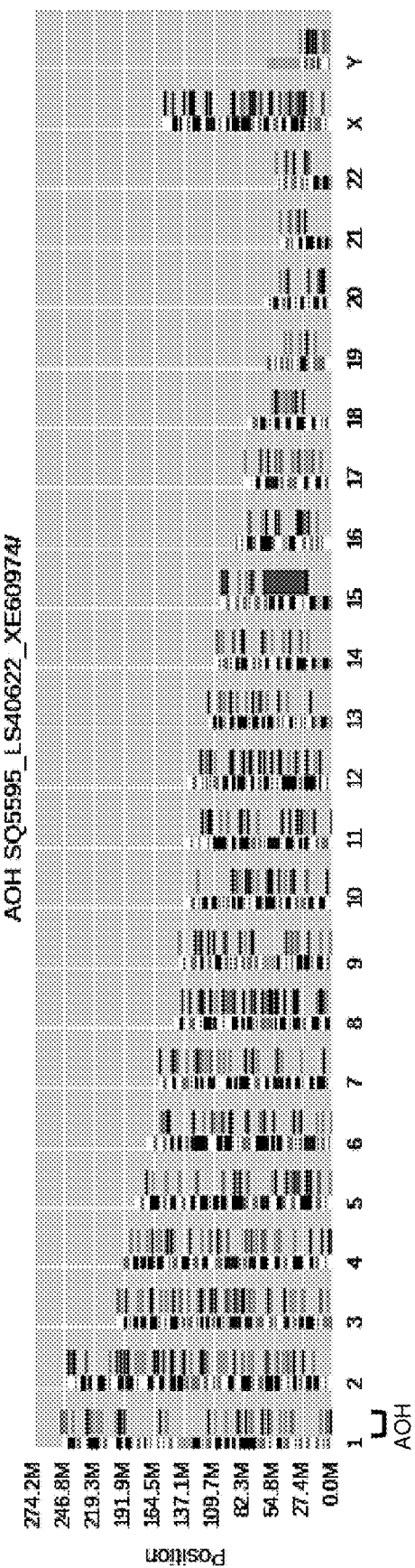
Figure 4C:
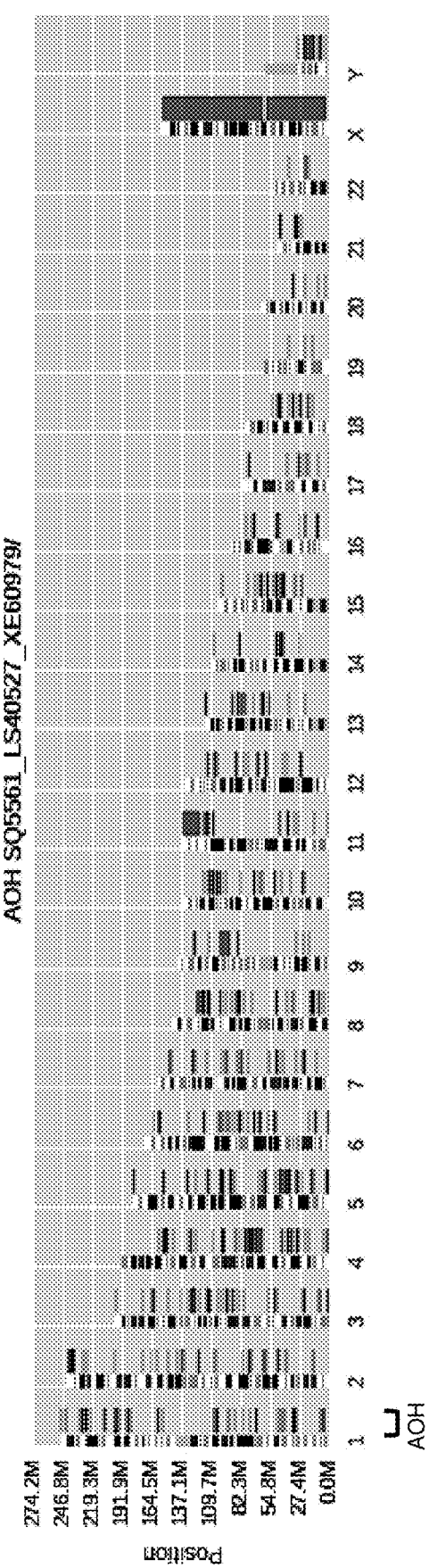
Figure 4D:
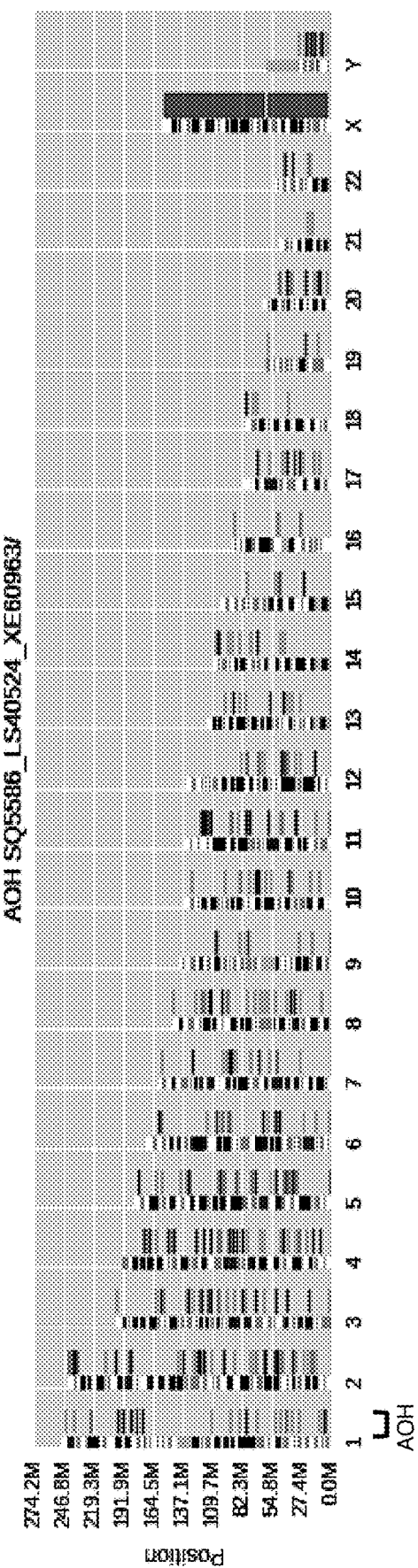
Figure 5A:
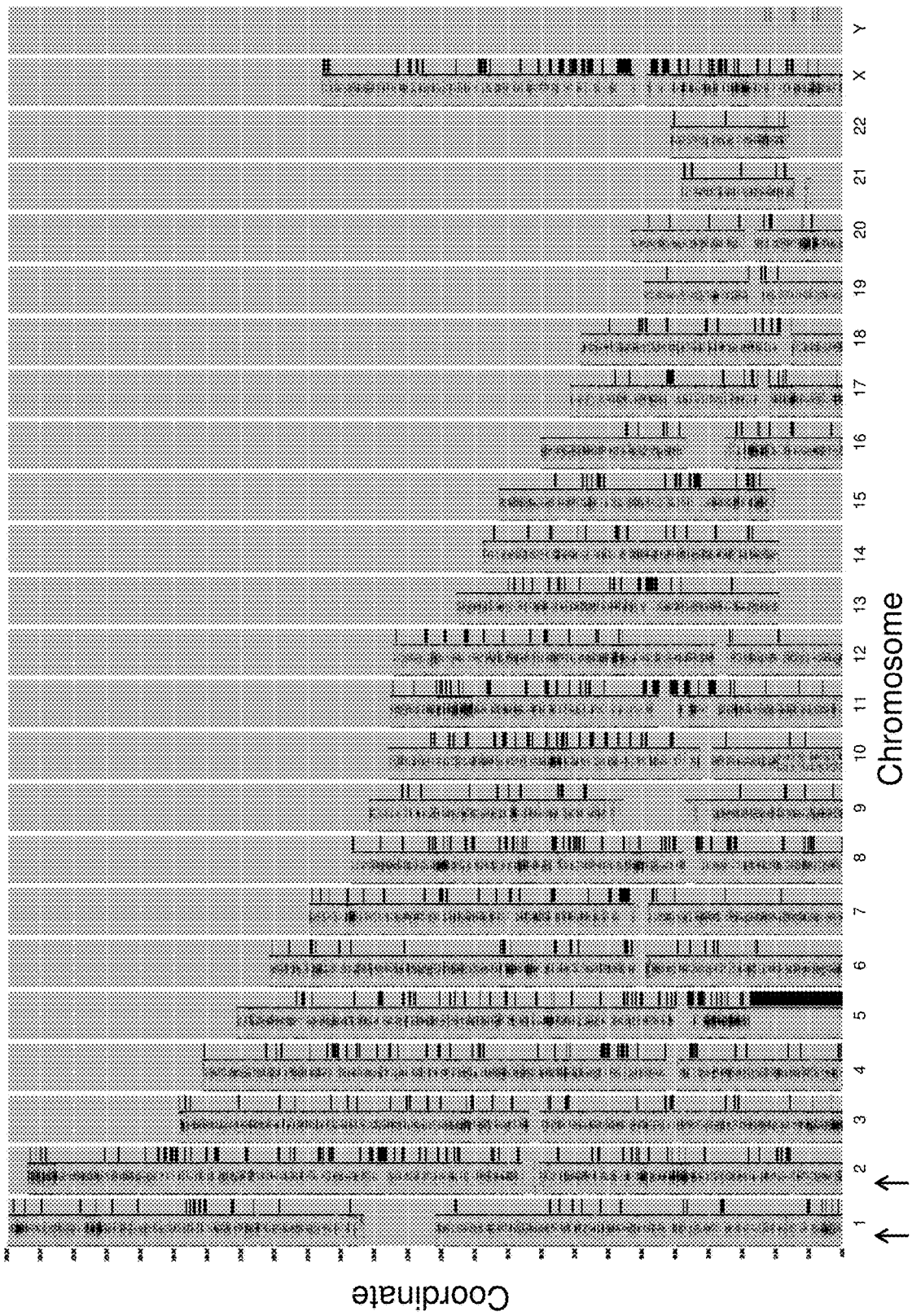
FIGS. 5A and 5B shows a graphical illustration of allele balance determinations and AOH calls for portions of a subject's genome. Chromosome numbers are indicated on the x-axis and above each shaded column. Chromosome positions are indicated on the Y-axis. Each chromosome column includes allele balance determinations (micro dots, left side of each chromosome column) and AOH calls (horizontal shaded lines, right side of each column). Allele balances are presented within a range between a normalized value of 0 and 1. In this example, the allele balance for normalcy (i.e., presence of heterozygosity, i.e., no AOH) is expected to occur in all three states of zygosity (values near 0, 0.5 and 1). Large stretches of homozygosity are indicated by large blocks of sites which allele balances are homozygous reference (0) or homozygous alternate (1). Additionally, allele balance is indicative of copy number and its expected value is a multiple of 1/(copy number).
Figure 5B:
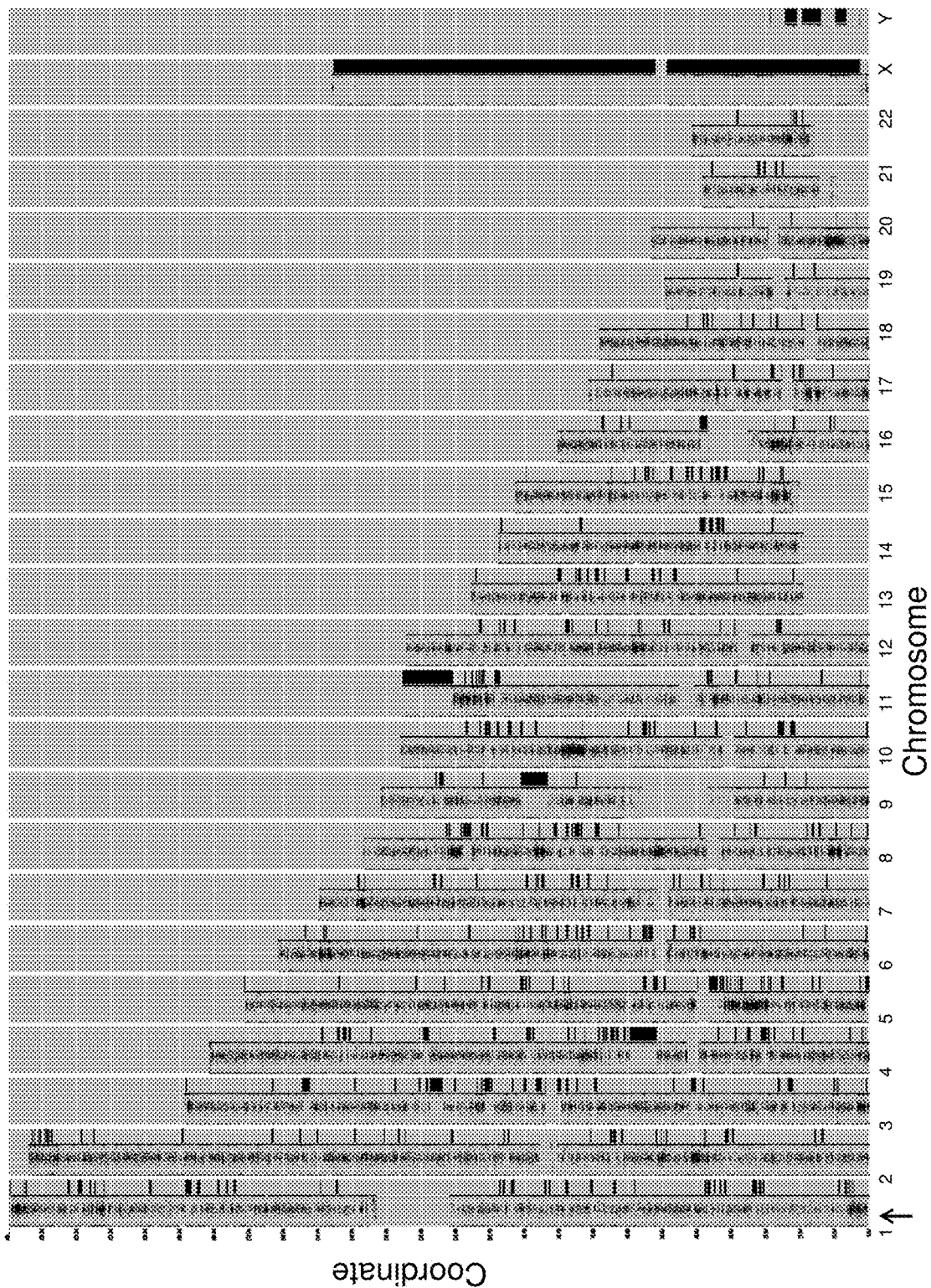
Figure 6A:
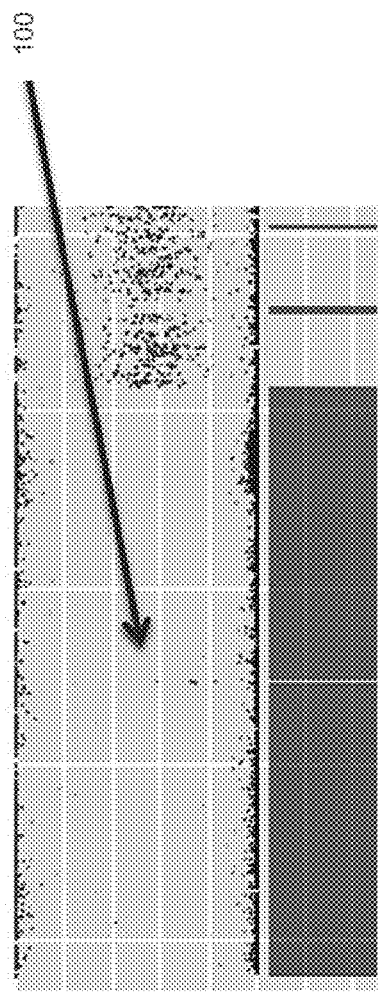
FIG. 6A shows an embodiment of a method of removing technical artifacts introduced by reads that introduce error. Some sites on the genome do not exhibit Hardy-Weinberg Equilibrium, and do not behave as expected. Many of these sites are due to cryptic paralogues, sequences missing from the genome which reads are aligned to a single locus. These sites can be bioinformatically detected and removed from an analysis by empirically detecting sites which do not exhibit Hardy-Weinberg Equilibrium. Arrow 100 indicates heterozygous variants that break up an AOH segment.
Figure 6B:
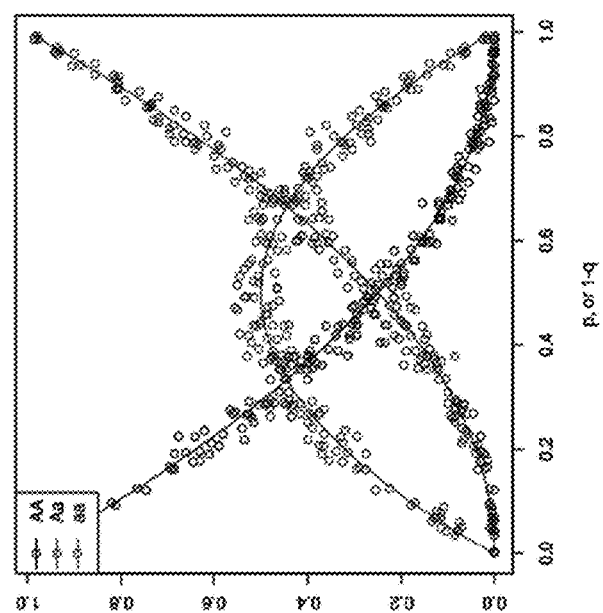
FIG. 6B shows that HMM is configured to tolerate some errors: P(gt=het|aoh=True=0.001, but filtering noise is ideal.
Figures 7A, 7B, 7C:
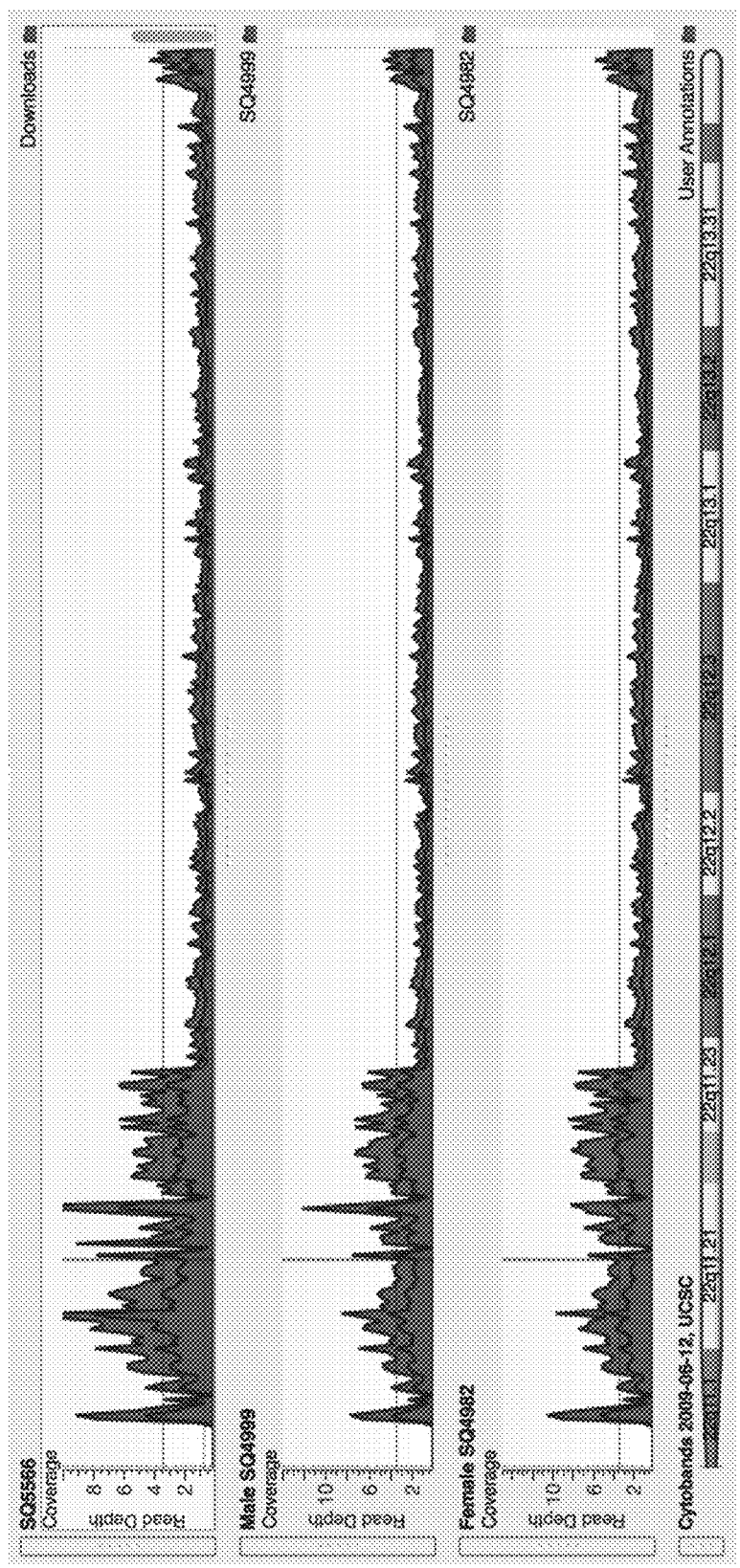
FIG. 7A, FIG. 7B, and FIG. 7C show raw coverage values for large (3-4 MB) duplication. (Mb (=Mbp)=mega base pairs=1,000,000 bp) The top sample chart (FIG. 7A) contains the duplication, and the middle (FIG. 7B) and bottom (FIG. 7C) sample charts are normal. A horizontal line is drawn for all sample charts at the same value (~3) to serve as a comparison point. It is clear from the figure that the number of reads which align within the top sample chart are significantly higher were the known duplication is. Additionally, the ratio of coverage is about 3:2, indicating that there was a gain of precisely 1 copy of the region. (SQ5566-+der(22)t(11;22)(q23.3;q11.2)~3-4 Mb gain).
Figures 8A, 8B, 8C:
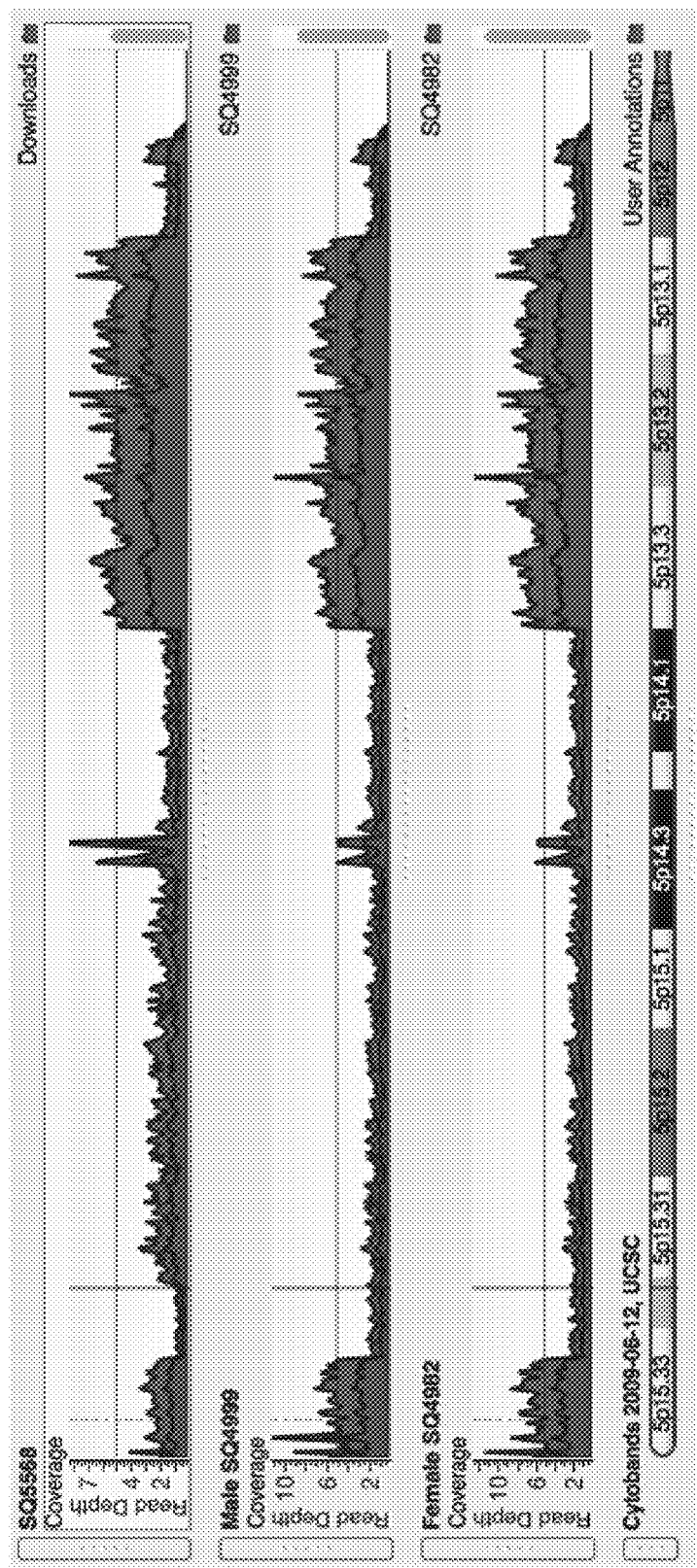
FIG. 8A, FIG. 8B, and FIG. 8C show a 5.9 MB deletion followed by a 15.3 MB gain. The top sample chart (FIG. 8A) contains the deletion and duplication, and the middle (FIG. 8B) and bottom (FIG. 8C) sample charts are normal. A horizontal line is drawn for all sample charts at the same value (~5) to serve as a comparison point. It is clear from the figure that the number of reads which align within the top sample chart are significantly lower at the known deletion, and significantly higher at the known duplication. (SQ5568-der(5)del(5)(p15.32)dup(5)(p14.3p15.32)~5.9 Mb terminal loss and ~15.3 Mb interstitial gain).
Figures 9A, 9B, 9C:
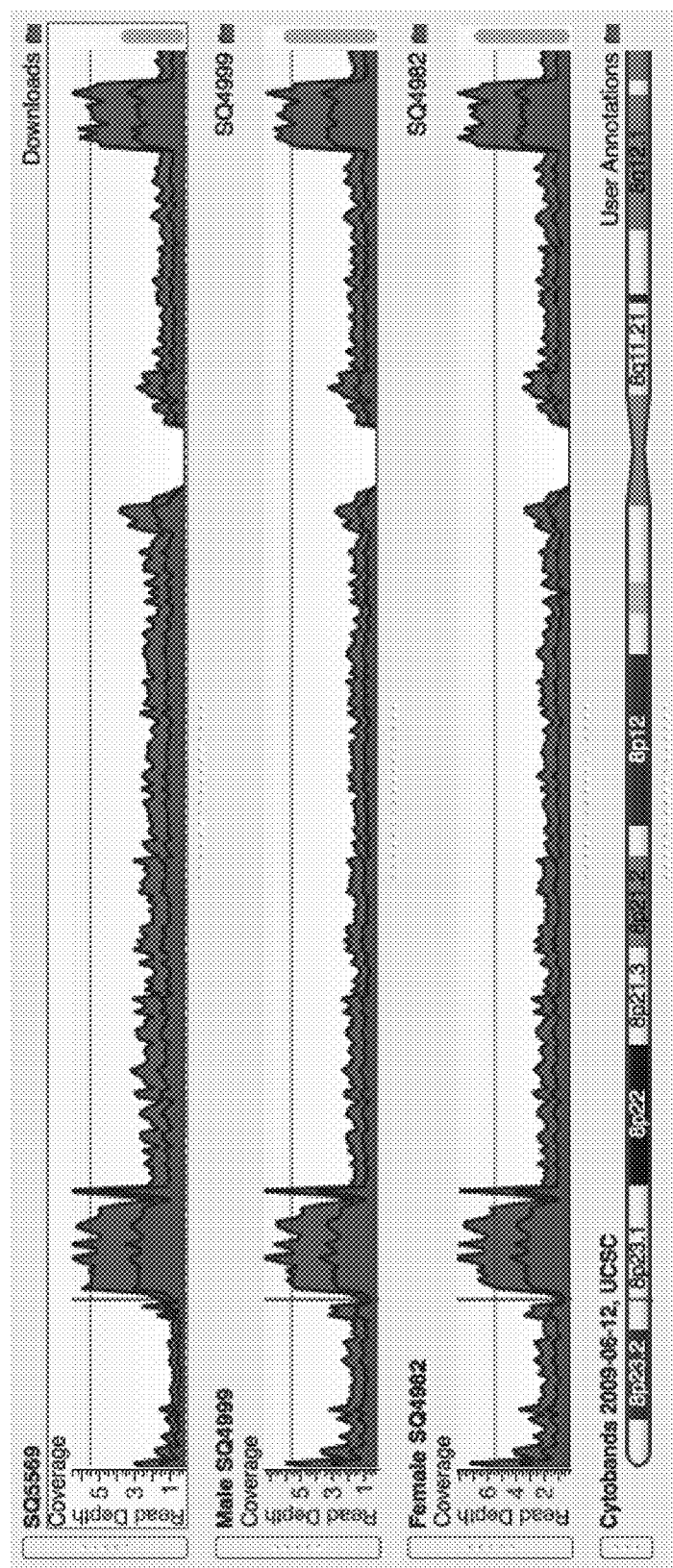
FIG. 9A, FIG. 9B, and FIG. 9C show a deletion followed by a duplication. The top sample chart (FIG. 9A) contains the deletion and duplication, and the middle (FIG. 9B) and bottom (FIG. 9C) sample charts are normal. A horizontal line is drawn for all sample charts at the same value (~6) to serve as a comparison point. It is clear from the plot that the number of reads which align within the top sample chart are significantly lower at the known deletion, and significantly higher at the known duplication. (SQ5569-der(8)del(8) (p23.1)dup(8)(p11.1p23.1))

Next generation sequencing (NGS) can be used to sequence nucleic acids for a complete human genome, which requires large amounts of expensive reagents, large amounts of digital storage space, massive amounts of CPU intensive analysis, and a considerable amount of labor and time. Such traditional gold standard NGS techniques are often too slow, too laborious and too expensive to screen hundreds or thousands of subjects for a genetic variation. The novel methods, processes and systems described herein are commercially valuable, because they reduce costs (e.g., reagent costs), implementation and processing time, CPU burden, memory storage, and manpower typically required for traditional gold standard techniques, and thereby provide a novel more efficient, faster method to determine the presence or absence of genetic variations by quickly and efficiently analyzing the entire genome of one or more subjects. The methods, processes and systems described herein are, in part, computer implemented methods which solve problems that arise during the generation and electronic analysis of NGS generated sequence reads. Accordingly, methods, processes and systems presented herein have no analog in the pre-Internet/pre-computer world.

Subjects

A subject can be any living or non-living organism, including but not limited to a human, non-human animal, plant, bacterium, fungus, virus or protist. A subject may be any age (e.g., an embryo, a fetus, infant, child, adult). A subject can be of any sex (e.g., male, female, or combination thereof). A subject may be pregnant. In some embodiments a subject is a mammal. In some embodiments a subject is a human subject. A subject can be a patient (e.g., a human patient). In some embodiments a subject is suspected of having a genetic variation or a disease or condition associated with a genetic variation.

Samples

Provided herein are methods and compositions for analyzing a sample. A sample (e.g., a sample comprising nucleic acid) can be obtained from a suitable subject. A sample can be isolated or obtained directly from a subject or part thereof. In some embodiments a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. A fluid or tissue sample from which nucleic acid is extracted may be acellular (e.g., cell-free). Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid).

In some embodiments a sample comprises nucleic acid, or fragments thereof. In certain embodiments a sample comprises nucleic acid representing a portion of, or all of a subject's genome. A genome of a subject often refers to the entire nuclear content of a subject's cells, which includes an entire complement of chromosomes present in a subject. In some embodiments a genome of a subject comprises substantially all nucleic acids (e.g., DNA) present in the nucleus of a plurality of cells obtained from a subject.

In some embodiments a sample comprises a mixture of nucleic acids. A mixture of nucleic acids can comprise two or more nucleic acid species having different nucleotide sequences, different fragment lengths, different origins (e.g., genomic origins, cell or tissue origins, subject origins, the like or combinations thereof), or combinations thereof. Accordingly, a sample can comprise nucleic acids obtained from one or more subjects. For example, a sample may comprise nucleic acids (e.g., a library of nucleic acids) obtained from one subject or from 1 or more, 2 or more, 3 or more, 4 or more, 5 or more, 6 or more, 7 or more, 8 or more, 9 or more, 10 or more, 11 or more, 12 or more, 13 or more, 14 or more, 15 or more, 16 or more, 17 or more, 18 or more, 19 or more, or 20 or more subjects. Samples provided for processes or methods described herein may comprise nucleic acids from 1 to 1000, 1 to 500, 1 to 200, 1 to 100, 1 to 50, 1 to 20 or 1 to 10 subjects. In some embodiments a sample comprises nucleic acid obtained from a single subject.

Nucleic Acids & Genes

The terms "nucleic acid" refers to one or more nucleic acids, non-limiting examples of which include DNA, complementary DNA (cDNA), genomic DNA (gDNA), RNA (e.g., message RNA (mRNA), short inhibitory RNA (siRNA), ribosomal RNA (rRNA), tRNA, microRNA, and/or analogs of DNA or RNA (e.g., nucleic acids containing base analogs, sugar analogs and/or a non-native backbone, the like and known analogs of natural nucleotides that can function in a similar manner as naturally occurring nucleotides), RNA/DNA hybrids and polyamide nucleic acids (PNAs), or combinations thereof, all of which can be in single- or double-stranded form. In some embodiments nucleic acid refers to genomic DNA. Nucleic acids may be single or double stranded. A nucleic acid can be of any length of 2 or more, 3 or more, 4 or more or 5 or more contiguous nucleotides. A nucleic acid can comprise a specific 5' to 3' order of nucleotides known in the art as a sequence (e.g., a nucleic acid sequence, e.g., a sequence).

A nucleic acid may be naturally occurring and/or may be synthesized, copied or altered (e.g., by a technician, scientist or one of skill in the art). For, example, a nucleic acid may be an amplicon. A nucleic acid may be from a nucleic acid library, such as a gDNA, cDNA or RNA library, for example. A nucleic acid can be synthesized (e.g., chemically synthesized) or generated (e.g., by polymerase extension in vitro, e.g., by amplification, e.g., by PCR). A nucleic acid may be, or may be from, a plasmid, phage, virus, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. Oligonucleotides are relatively short nucleic acids. Oligonucleotides can be from about 2 to 150, 2 to 100, 2 to 50, or 2 to about 35 nucleic acids in length. In some embodiments oligonucleotides are single stranded. In certain embodiments oligonucleotides are primers. Primers are often configured to hybridize to a selected complementary nucleic acid and are configured to be extended by a polymerase after hybridizing. In certain embodiments primers are specifically configured to hybridize to targeted nucleic acids within a genome and are often configured to have specific melting temperatures, GC content and/or length. In some embodiments each primer of a set of primers are configured with the same or substantially similar melting temperature, GC content and/or length, wherein each primer of the set is configured to hybridize to a different targeted nucleic acid within a genome.

The genetic material of a subject often comprises one or more genes. In certain embodiments a gene comprises or consists of one or more nucleic acids. The term "gene" means the segment of DNA involved in producing a polypeptide chain and can include coding regions (e.g., exons), regions preceding and following the coding region (leader and trailer) involved in the transcription/translation of the gene product and the regulation of the transcription/translation, as well as intervening sequences (introns) between individual coding segments (exons). A gene may not necessarily produce a peptide or may produce a truncated or non-functional protein due to genetic variation in a gene sequence (e.g., mutations in coding and non-coding portions of a gene). For example, a non-functional gene can be a pseudogene. A gene, whether functional or non-functional, can often be identified by homology (e.g., percent identity) to a gene in a reference genome. In a diploid subject, a gene often comprises a pair of alleles (e.g., two alleles). Thus a method, system or process herein can be applied to one or both alleles of a gene. In some embodiments a method, system or process herein is applied to each allele of a gene.

In certain embodiments a gene comprises a genetic variation or is suspected of comprising a known genetic variation. In certain embodiments a gene comprises, or is suspected of having, a genetic variation associated with a disease, condition or disorder. In certain embodiments a gene comprises, or is suspected of having a genetic variation associated with a subject predisposed to a disease, condition or disorder.

In certain embodiments two or more nucleic acid sequences are identical or substantially identical. Substantially identical refers to two nucleic acid sequences that have a percent identity of at least 70%, at least 75%, at least 80%, at least 85%, at least 90% or at least 95%. The term "percent identical", "% identical" or "percent identity" refers to sequence identity between two polynucleotide sequences. Identity can be determined by comparing a position in each sequence which may be aligned for purposes of comparison. When an equivalent position in the compared sequences is occupied by the same nucleotide, then the molecules are identical at that position. When the equivalent site is occupied by the same or a similar nucleotide, then the molecules can be referred to as homologous (similar) at that position.

Expression as a percentage of homology, similarity, or identity refers to a function of the number of identical or similar nucleotides at positions shared by the compared sequences. Expression as a percentage of homology, similarity, or identity refers to a function of the number of identical or similar nucleotides at positions shared by the compared sequences. Any suitable alignment algorithm and/or program may be used to determine percent identity.

Other non-limiting examples of techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. In some embodiments an alignment program that permits gaps in the sequence is utilized to align the sequences. The Smith-Waterman is one type of algorithm that permits gaps in sequence alignments. See Meth. Mol. Biol. 70:173-187 (1997). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Nucleic Acid Isolation & Purification

Nucleic acid may be derived, isolated, extracted, purified or partially purified from one or more subjects, one or more samples or one or more sources using suitable methods known in the art. In certain embodiments a gene, or portions thereof, is isolated from, purified from, extracted from or derived from one or more subjects. Any suitable method can be used for isolating, extracting and/or purifying nucleic acid.

The term "isolated" as used herein refers to nucleic acid removed from its original environment (e.g., the natural environment if it is naturally occurring, or a host cell if expressed exogenously), and thus is altered by human intervention from its original environment. The term "isolated nucleic acid" as used herein can refer to a nucleic acid removed from a subject (e.g., a human subject). An isolated nucleic acid can be provided with fewer non-nucleic acid components (e.g., protein, lipid) than the amount of components present in a source sample. A composition comprising isolated nucleic acid can be about 50% to greater than 99% free of non-nucleic acid components. A composition comprising isolated nucleic acid can be about 90%, 91%, 92%, 93%, 94%, 95%, 96%, 97%, 98%, 99% or greater than 99% free of non-nucleic acid components. The term "purified" as used herein can refer to a nucleic acid provided that contains fewer non-nucleic acid components (e.g., protein, lipid, carbohydrate, salts, buffers, detergents, and the like, or combinations thereof) than the amount of non-nucleic acid components present prior to subjecting the nucleic acid to a purification procedure. A composition comprising purified nucleic acid may be at least about 60%, 70%, 80%, 81%, 82%, 83%, 84%, 85%, 86%, 87%, 88%, 89%, 90%, 91%, 92%, 93%, 94%, 95%, 96%, 97%, 98%, 99% or greater than 99% free of other non-nucleic acid components. A composition comprising purified nucleic acid may comprise at least 80%, 81%, 82%, 83%, 84%, 85%, 86%, 87%, 88%, 89%, 90%, 91%, 92%, 93%, 94%, 95%, 96%, 97%, 98%, 99% or greater than 99% of the total nucleic acid present in a sample prior to application of a purification method.

Nucleic Acid Sequencing

In certain embodiments nucleic acids (e.g., amplicons, nucleic acids of a library, captured nucleic acids) are analyzed by a process comprising nucleic acid sequencing. In some embodiments nucleic acids may be sequenced, thereby producing sequence reads. In some embodiments a portion of a genome, chromosome or gene is sequenced. In certain embodiments of the methods, processes and systems described herein, partial sequences of a genome, chromosome or gene are obtained. In some embodiments, an entire genome is subjected to sequencing method where nucleic acids sequence reads are generated from the entire genome. In such embodiments where reads are obtained from an entire genome, the reads may represent nucleic acid sequences of a portion of the entire genome.

Any suitable method of sequencing nucleic acids can be used to generate sequence reads, non-limiting examples of which include Maxim & Gilbert, Sanger, chain-termination methods, sequencing by synthesis, sequencing by ligation, sequencing by mass spectrometry, microscopy-based techniques, the like or combinations thereof. In preferred embodiments a high-throughput sequencing method (e.g., a next generation sequencing (NGS) method) is used. In certain embodiments high-throughput sequencing methods generally involve a plurality of nucleic acid molecules and/or clonally amplified nucleic acids that are simultaneously sequenced in a massively parallel fashion, sometimes within a flow cell. NGS sequencing methods (e.g., including $2^{nd}$, $3^{rd}$ and $4^{th}$ generation methods, etc.) are capable of sequencing DNA in a massively parallel fashion and can be used for methods described herein. NGS and "massively parallel sequencing" (MPS) methods are collectively referred to herein as NGS sequencing. Any suitable MPS or next generation sequencing method, system or technology platform for conducting methods described herein can be used to obtain sequencing reads, non-limiting examples of which include Illumina/Solex/HiSeq (e.g., Illumina's Genome Analyzer; Genome Analyzer II; HISEQ 2000; HISEQ 2500, SOLiD, Roche/454, PACBIO, SMRT, Helicos True Single Molecule Sequencing, Ion Torrent and Ion semiconductor-based sequencing, WildFire, 5500, 5500xl W and/or 5500xl W Genetic Analyzer based technologies (e.g., as developed and sold by Life Technologies), Polony sequencing; Pyrosequencing, Massively Parallel Signature Sequencing, RNA polymerase (RNAP) sequencing, IBS methods, LaserGen systems and methods, chemical-sensitive field effect transistor (CHEMFET) array, electron microscopy-based sequencing, nanoball sequencing, sequencing-by-synthesis, sequencing by ligation, sequencing-by-hybridization, the like or variations thereof. Additional sequencing technologies that include the use of developing nucleic acid imaging technologies (e.g., transmission electron microscopy (TEM) and atomic force microscopy (AFM)), also are contemplated herein. In preferred embodiments, methods, processes and systems described herein utilize an NGS method that generates only single-end reads.

In some embodiments NGS sequencing methods utilize a targeted approach, where sequence reads are generated from primers configured and/or designed to target (e.g., hybridize to) specific sequences within a genome, chromosome, or gene. Specific sequences within a genome, chromosome, or gene are sometimes referred to herein as targeted genomic regions. In certain embodiments sequence reads are not obtained by a method comprising paired-end sequencing. In certain embodiments, methods, processes and systems described herein do not comprise generating paired-end sequence reads or analysis of paired-end sequence reads. In some embodiments, methods, processes and systems described herein utilize an NGS method that produces single-end reads using a targeted approach. NGS methods that produce single-end reads using a targeted approach as described herein are less expensive, faster and require less CPU time for analysis when compared to whole genome sequences methods using a paired-end sequencing approach.

Sequence Reads

Subjecting a nucleic acid to a sequencing method often provides sequence reads. The term "sequence read" is used synonymously with the term "read", and grammatical variations thereof. In certain embodiments sequence reads are obtained by an MPS or NGS method. Reads generally are a representation of a nucleotide sequence of a physical nucleic acid. For example, in a read containing an ATGC depiction of a sequence, "A" represents an adenine nucleotide, "T" represents a thymine nucleotide, "G" represents a guanine nucleotide and "C" represents a cytosine nucleotide, in a physical nucleic acid. Accordingly, a read is short nucleotide sequence produced by a sequencing process described herein or known in the art. A read is often derived from extension of a primer by a polymerase in a 5' to 3' direction, wherein the primer (or portion thereof) anneals specifically to a template nucleic acid within a genome. Therefore a read includes nucleic acid sequence derived from the template nucleic acid and located 3' of a primer portion of a read. Targeted primer sequences used herein are selected to specifically anneal near a loci of a common polymorphism within a subject's genome. Accordingly, when a primer is extended during a sequencing process used herein, a read is produced which includes sequence information for a common polymorphism located 3' of the primer portion of the read. In certain embodiments the primer portion of a read can anneal to one or multiple locations within a genome. For example, where a genome is diploid, at least two reads will be produced from the same primer, each representing the nucleic acid sequence of one of the two alleles present in the diploid genome. Accordingly, the nucleic acid sequence of reads derived from the same primer may be the same or different. For example, where a read includes the sequence of a single nucleotide polymorphism (SNP) of a subject who is heterozygous for the SNP, two different reads are generated which differ by a single nucleotide at the loci of the SNP. In certain embodiments herein, the sequence information obtained from reads generated at the loci of a common polymorphism or SNP is exploited to determine an allele balance at the site of the common polymorphism. For example, where multiple copies of a template are present, (e.g., in the case of a copy number variation (CNV)), multiple reads will be generated for a loci that includes a polymorphism, thereby skewing the expected allele balance.

The term "overlapping reads", as used herein, refers to two sequence reads obtained from substantially different primers where a portion of the nucleic sequence of each of the two reads is obtained from the same nucleic acid template. The portion of the nucleic sequence of overlapping reads that is obtained from the same nucleic acid template may be obtained from either strand of the same template. For example a portion of the sequence of a first read may be substantially identical to the reverse complement of a second read, where the two reads are generated from different primers. Such reads are said to be overlapping reads.

In some embodiments sequence reads are non-overlapping reads. The term "non-overlapping sequence reads" as used herein refers to two sequence reads obtained from substantially different primers where the nucleic sequence of each read does not include a portion obtained from the same nucleic acid template (e.g., either strand of a template nucleic acid). In certain embodiments at least 75%, at least 80%, at least 85%, at least 90%, at least 95%, at least 96%, at least 97%, at least 98%, at least 99%, or substantially all of the sequence reads generated by, or obtained or provided for, a method, process or system herein, comprise or consist of non-overlapping reads. In certain embodiments at least 75%, at least 80%, at least 85%, at least 90%, at least 95%, at least 96%, at least 97%, at least 98%, at least 99% or substantially all of the single-end sequence reads generated by, or obtained or provided for, a method, process or system herein, comprise or consist of non-overlapping reads.

In certain embodiments sequence reads are generated. Sequence reads can be generated by a suitable nucleic acid sequencing method. In certain embodiments sequence reads are obtained or provided. Sequence reads can be obtained directly (e.g., received directly from a sequencing apparatus), or indirectly from a sequencing apparatus. In some embodiments reads are obtained from, or provided by a third party. In some embodiments sequence reads are obtained or provided in the form of a non-transitory computer-readable storage medium. In some embodiments sequence reads are obtained or provided in the form of one or more computer-readable files.

The length of a sequence read is often associated with a particular sequencing technology. High-throughput methods and/or next generation sequencing, for example, provide sequence reads that can vary in size from tens to hundreds of nucleotides (nt). Methods and processes described herein comprise the generation of single end reads. In some embodiments sequence reads are of a mean, median, average or absolute length of about 10 nt to about 1000 nt long. In some embodiments the nominal, average, mean or absolute length of single-end reads is about 10 nucleotides (nt) to about 1000 nucleotides, about 10 nucleotides to about 500 nucleotides, about 10 nucleotides to about 250 nucleotides, about 10 nucleotides to about 200 nucleotides, about 10 nucleotides to about 150 nucleotides, about 15 nucleotides to about 300 nucleotides, about 15 nucleotides to about 250 nucleotides, about 15 nucleotides or about 200 nucleotides or about 15 nucleotides or about 100 contiguous nucleotides in length. In certain embodiments the nominal, average, mean or absolute length of a single-end read is less than 500 nt, less than 400 nt, less than 300 nt, less than 250 nt, less than 200 nt, less than 150 nt, less than 100 nt, or less than 50 nt. In certain embodiments the nominal, average, mean or absolute length of a single-end read is selected from lengths consisting of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 and 50 nucleotides or more.

In certain embodiments a substantial amount of the nucleic acid sequences of single-end reads produced by a method, process or system herein do not overlap. The term "substantial" and "substantially", as used herein with reference to an amount or quantitative value, means at least 75%. In certain embodiments a substantial amount is at least 80%, at least 85%, at least 90%, or at least 95% of the referenced amount or value. Accordingly, in certain embodiments, a substantial amount or all of the single-end reads generated, obtained or used for a method, process or system herein are non-overlapping reads.

The term, "sequence information" refers to all or a portion of a nucleotide sequence of a genome. In some embodiments, sequence information can include a genomic location (e.g., genomic locus, chromosome coordinate, polymorphism coordinate, plus or minus strand, the like, or combinations there), an identifier (e.g., name, designation or unique identifier, e.g., for an identifier for a polymorphism, gene, exon, intron, regulatory region, transposon, or region of a genome) and/or a nucleic acid sequence. In some embodiments sequence information comprises a nucleotide sequence of an intron/exon junction. In some embodiments sequence information comprises the identity (e.g., A, T, G or C) and location of one or more genetic variations within a genome. In some embodiments sequence information comprises the identity (e.g., A, T, G or C) and location of a single nucleotide (e.g., a SNP) within a genome (e.g., within a genomic sequence). In certain embodiments a read (e.g., a mapped read) comprises sequence information. For example, a mapped or aligned read can provide information as to identity and location of a particular nucleotide, or nucleic acid sequence, present at a specific location within a genome. In some embodiments a read comprises sequence information for a polymorphism, thereby providing the identity of a nucleotide (e.g., A, T, G or C) present at a genomic location where a known polymorphism resides. In some embodiments a read comprises sequence information for a particular SNP, thereby providing the identity of a nucleotide (e.g., A, T, G or C) present at a genomic location where the particular SNP was previously identified. In some embodiments sequence information can indicate the absence or deletion of one or more nucleotides from a portion of a genome (e.g., as compared to a reference genome or reference sequence). In certain embodiments targeted primers (e.g., targeted probes) used for a method herein are configured to generate a read that includes sequence information for an intron/exon junction. Accordingly, in certain embodiments, the sequence information of a read can indicate the presence or absence of an intron/exon junction within a genome of a subject.

A mixture of a plurality of relatively short reads can be transformed by processes described herein into a representation of a genome present in subject. A mixture of relatively short reads can be transformed into a representation of one or more copy number variations within a genome, for example. Reads of a mixture of nucleic acids from multiples subjects can be transformed into a representation of a genome, or portion thereof, for each of the multiple subjects.

In certain embodiments sequence reads are generated or obtained from an entire genome of a subject. In some embodiments reads that are generated or obtained from an entire genome of a subject collectively represent portions of the nucleic acid sequence of every chromosome of the subject's genome. In some embodiments reads that are generated or obtained from an entire genome of a subject collectively represent portions of the nucleic acid sequence of substantially all chromosomes of a subject's genome. In some embodiments reads that are generated or obtained from an entire genome of a subject collectively represent portions of the nucleic acid sequence of every autosome of a subject's genome.

In certain embodiments reads (e.g., single-end reads) generated or obtained by a method herein represent less than 30%, less than 25%, less than 20%, less than 15%, less than 10%, less than 9%, less than 8%, less than 7%, less than 6%, less than 5%, less than 4%, less than 3%, less than 20%, or less than 1% of the nucleic acid sequence of an entire genome. In certain embodiments single-end reads are generated from an entire genome where the reads represent less than 5%, less than 4%, less than 20% or less than 1% of the nucleic acid sequence of an entire genome. In certain embodiments single-end reads are generated from an entire genome where the reads represent between about 1% and 5%, between about 1% and 4%, between about 1% and 3%, or between about 1% and 2% of the nucleic acid sequence of an entire genome. In certain embodiments single-end reads are generated from an entire genome where the reads represent between about 0.5% and 5%, between about 0.5% and 4%, between about 0.5% and 3%, between about 0.5% and 2%, or between about 0.5% and 1% of the nucleic acid sequence of an entire genome.

In some embodiments a portion of a genome is sequenced. In certain embodiments sequence reads are generated or obtained from a portion of an entire genome of a subject. For example, sequence reads are sometimes generated from 1 to 44, 1 to 30, 1 to 20, or 1 to 10 chromosomes of a subject's genome. In some embodiments reads that are generated or obtained from a portion of a genome of a subject collectively represent portions of the nucleic acid sequence of about 40 chromosomes or less, about 30 chromosomes or less, or about 20 chromosomes or less, of a subject's genome. In some embodiments sequence reads are generated from 1, 2, 3, or 4 chromosomes of a subject's genome.

In certain embodiments targeted primers (e.g., targeted probes) that are used for a method, process or system described herein are configured to hybridize to a plurality of target sequences (target sites) of a genome (e.g., an entire genome) wherein each target sequence is separated by an average, median or absolute distance (i.e., distance of contiguous nucleotides of a nucleic acid) of at least 2000 base pairs (bp), at least 3000 bp, at least 4000 bp, at least 5000 bp, at least 6000 bp, at least 7000 bp, at least 8000 bp, at least 9000 bp, at least 10,000 bp, at least 12,000 bp, at least 15,000 bp, or at least 20,000 bp. In certain embodiments a distance between target sequences, target sites, common polymorphisms or mapped reads refers to a distance as measured in contiguous nucleotides (nt) or base pairs (bp) for a single strand or double strand of nucleic acid.

In certain embodiments a set of reads comprises or consists of a plurality of reads, wherein each of the plurality of reads represents a non-overlapping sequence of a portion of a genome (e.g., a portion of an entire genome) and the average, median or absolute distance between any two reads of the set (e.g., when aligned with a genome) is at least 2000 bp, at least 3000 bp, at least 4000 bp, at least 5000 bp, at least 6000 bp, at least 7000 bp, at least 8000 bp, at least 9000 bp, at least 10,000 bp, at least 12,000 bp, at least 15,000 bp, or at least 20,000 bp.

In certain embodiments a set of single-end reads are obtained or generated wherein the set of reads comprises sequence information derived from an entire genome of a subject, and (i) the reads represent less than 20%, less than 10%, less than 5% or less than 2% coverage of an entire genome, and (ii) the average distance between any two reads of the set is at least 2000 bp. In certain embodiments a set of reads comprises between about 100,000 and 600,000 reads, or between about 300,000 and about 500,000 reads where the reads are substantially non-overlapping reads. In certain embodiments a set of reads comprises about 600,000 reads or less, about 550,000 reads or less, about 500,000 reads or less, about 400,000 reads or less, about 300,000 reads or less, or about 200,000 reads or less. In certain embodiments a set of reads comprises at least 100,000, at least 200,000, at least 250,000, at least 300,000, at least 350,000, at least 400,000, at least 450,000, at least 500,000, at least 550,000, or at least 600,000 non-overlapping reads.

Mapping Reads

In some embodiments sequence reads are aligned and/or mapped to a reference genome.

In some embodiments a suitable mapping method, process or algorithm is used to map reads. Certain aspects of mapping processes are described hereafter. Mapping nucleotide sequence reads can be performed in a number of ways, and often comprises alignment of sequence reads, or portions thereof, with a reference sequence or a reference genome. As used herein, the terms "aligned", "alignment", or "aligning" refer to two or more nucleic acid sequences that can be identified as a match (e.g., 100% identity) or partial match. In some cases, an alignment is less than a 100% identity (e.g., non-perfect match, partial match, partial alignment). In some embodiments an acceptable alignment of two nucleic acids comprises at least a 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76% or 75% identity. In certain embodiments an alignment method used for a method, process or system described herein allows for at least one mismatch between a read and a reference sequence. In certain embodiments a partial match allows for 1 to 10 mismatches, or 1, 2, 3, 4, 5, 6, 7, 8, 9 or 10 mismatches when aligning a read to a reference genome. Two or more sequences can be aligned using either strand. In certain embodiments a nucleic acid sequence is aligned with the reverse complement of another nucleic acid sequence. A sequence read that is aligned with a reference genome or reference sequence is often referred to as a mapped read.

As used herein, the term "reference genome" can refer to any particular known, sequenced or characterized genome, whether partial or complete, of any organism or virus which may be used to reference identified sequences from a subject. A reference genome can be a complete genome or a partial genome. A reference genome sometimes refers to a segment or portion of a reference genome (e.g., a chromosome or part thereof, e.g., one or more portions of a reference genome). Human genomes, human genome assemblies and/or genomes from any other organisms can be used as a reference genome. One or more human genomes, human genome assemblies as well as genomes of other organisms can be found online at the National Center for Biotechnology Information at http//www.ncbi.nlm.nih.gov/. In some embodiments a reference genome is the human genome reference sequence version GRCh37 (Church DM, S.V. (2011) PLoS Biol, 9 (7)), for example. In certain embodiments a reference genome often is an assembled or partially assembled genomic sequence from an individual or multiple individuals. In some embodiments a reference genome is an assembled or partially assembled genomic sequence from one or more human individuals.

In certain embodiments reads obtained herein are aligned or mapped to one or more reference sequences. The term "reference sequence" as used herein refers to one or more polynucleotide sequences obtained from a subject or sample wherein the reference sequence comprises known sequence information. In some embodiments a reference sample is obtained from one or more reference subjects substantially free of a genetic variation. In some embodiments a reference sample is obtained from one or more reference subjects comprising a known genetic variation (e.g., a know copy number variation, known polymorphism, known genetic variation or absence thereof). In some embodiments reads can be mapped and/or aligned with reference sequences or databases comprising reference sequences, non-limiting examples of which include GenBank, dbEST, dbSTS, EMBL (European Molecular Biology Laboratory) and DDBJ (DNA Databank of Japan).

Methods of aligning nucleic acid sequences are known and a suitable alignment method can be used for a method, system, process, module or program described herein. Alignments can be performed manually (e.g., for small projects), however such manual methods are impractical and not suitable for aligning reads generated by NGS methods due to the enormous amount of time and expense that would be required to do so. Accordingly, in certain embodiments of the methods, processes and systems described herein, sequence reads are aligned and/or mapped by a suitable computer implemented module, program, or algorithm, non-limiting examples of which include Efficient Local Alignment of Nucleotide Data (ELAND), BWA (Li H. and Durbin R. (2009)Bioinformatics 25, 1754-60), Novoalign [Novocraft (2010)], Bowtie (Langmead B, et al., (2009)Genome Biol. 10:R25), SOAP2 (Li R, et al., (2009)Bioinformatics 25, 1966-67), BFAST (Homer N, et al., (2009) PLoS ONE 4, e7767), GASSST (Rizk, G. and Lavenier, D. (2010) Bioinformatics 26, 2534-2540), and MPscan (Rivals E., et al. (2009)Lecture Notes in Computer Science 5724, 246-260), or the like. Sequence reads and/or paired-end reads can be mapped and/or aligned using a suitable short read alignment program. Non-limiting examples of short read alignment programs are BarraCUDA, BFAST, BLASTN, BLAST, BLAT, BLITZ, Bowtie (e.g., BOWTIE 1, BOWTIE 2), BWA (Li H, D.R., Fast and accurate short read alignment with Burrows-Wheeler transform. (2009), Bioinformatics, 26 (5), 589-95), CASHX, CUDA-EC, CUSHAW, CUSHAW2, drFAST, FASTA, ELAND, ERNE, GNUMAP, GEM, GensearchNGS, GMAP, Geneious Assembler, iSAAC, LAST, MAQ, mrFAST, mrsFAST, MOSAIK, MPscan, Novoalign, Novoalign3, NovoalignCS, Novocraft, NextGENe, Omixon, PALMapper, Partek, PASS, PerM, PROBEMATCH, QPalma, RazerS, REAL, cREAL, RMAP, rNA, RTG, Segemehl, SeqMap, Shrec, SHRiMP, SLIDER, SOAP, SOAP2, SOAP3, SOCS, SSAHA, SSAHA2, Stampy, SToRM, Subread, Subjunc, Taipan, UGENE, VelociMapper, TimeLogic, XpressAlign, ZOOM, the like, variations thereof or combinations thereof. Parameters and thresholds (e.g., a percent identity thresholds) for an acceptable alignment or match can be predetermined by a user, module or program. In some embodiments a mapping module or a machine or computer comprising a mapping module is required to provide mapped sequence reads. A mapping module often comprises a suitable mapping and/or alignment program or algorithm.

In some embodiments one or more sequence reads and/or information associated with a sequence read are stored on, obtained from and/or accessed from a computer-readable storage medium (e.g., memory (e.g., random access memory), a hard drive, static drive, jump drive, ROM, disc or the like) in a suitable computer-readable format. A computer-readable storage medium can be local or remote (e.g., housed on one or more remote servers or cloud-based system). In certain embodiments a computer-readable storage medium is a non-transitory computer-readable storage medium. Information stored on a computer-readable storage medium is sometimes referred to as a file or data file. A data file cam be in a suitable format, non-limiting examples of which include BAM, sorted BAM, SAM, SRF, FASTA, FASTQ, Gzip, the like, or combinations thereof.

In some embodiments a program herein is configured to instruct a microprocessor to obtain or retrieve one or more files from a store media. In some embodiments a program herein instructs a microprocessor to call a module and/or transfers data and/or information (e.g., files) to or from one or more modules (e.g., a database, a sequencer, an aligner, a mapping module, and the like). In some embodiments a program instructs a processor to call a module which creates new files and formats for input into another processing step.

Methods, processes and systems described herein can utilize sequence information obtained from reads of a subject's genome to identify the presence or absence of a copy number variation within a subject's genome, wherein the reads comprise sequence information for a plurality of known polymorphisms. In certain embodiments a plurality of targeted primers are used to obtain a plurality of reads, wherein each primer is configured to hybridize adjacent to a known polymorphism. Mapped reads derived from each targeted primer can provide sequence information for a given polymorphism, thereby providing the identity of one or more nucleotides (e.g., A (adenine), C (cytosine), G (guanine) or T (thymine)) at a specific genomic locus where a known common polymorphism is expected to reside. In certain embodiments, methods, processes and systems described herein employ the use of at least 100,000, at least 200,000, at least 300,000, at least 400,000, at least 500,000, at least 600,000, at least 700,000, at least 800,000, at least 900,000, at least 1,000,000, at least 1,500,000 or at least 2,000,000 targeted primers, wherein each targeted primer is configured to obtain sequence information for a different common polymorphism. Accordingly, in certain embodiments, reads obtained by a method, process, or system described herein comprise sequence information for between about 100,000 and 2,000,000, between about 100,000 and 800,000, between about 100,000 and 500,000, or between about 200,000 and 600,000 different common polymorphisms in a genome. In certain embodiments reads obtained by a method, process, or system described herein comprise sequence information for at least 100,000, at least 200,000, at least 300,000, at least 400,000, at least 500,000, at least 600,000, at least 700,000, at least 800,000, at least 900,000, at least 1,000,000, at least 1,500,000 or at least 2,000,000 different common polymorphisms in a genome. In certain embodiments reads obtained by a method, process, or system described herein comprise sequence information for less than 800,000, less than 700,000, less than 600,000, less than 500,000, less than 400,000, or less than 300,000 different common polymorphisms in a genome.

In certain embodiments a common polymorphism is known within the human population. A common polymorphism is sometimes a single nucleotide polymorphism (SNP). In some embodiments a common polymorphism includes a contiguous stretch of 2, 3, 4, 5 or more nucleotides at a particular loci of a genome with known polymorph variants. A common polymorphism may include 2, 3, 4 or more SNPs within a contiguous portion of a genome (e.g., a contiguous portion of 3 bp to 500 bp). Accordingly, a read can include sequence information for 1 to 100, 1 to 50, or 1 to 5 SNPs. In some embodiments a read includes sequence information for a single SNP.

In some embodiments the genomic locus and relative frequency of occurrence (allele frequency) of a particular sequence variant (allele, haplotype, and/or genotype) of a common polymorphism is known within a population or subpopulation of subjects. Accordingly, an allele frequency that is known or obtained for a particular common polymorphism within a defined population of subjects is referred to herein as a "population allele frequency", "reference allele frequency" or simply as an "allele frequency". In certain embodiments an allele frequency is determined or provided for one or more, or a plurality of common polymorphisms. An allele frequency can be determined by any suitable method. In some embodiments an allele frequency is determined according to a distribution function. Any suitable distribution function can be used to determine an allele frequency for a given common polymorphism. Non-limiting examples of distribution functions include a probability function, probability distribution function, probability density function (PDF), a kernel density function (kernel density estimation), a cumulative distribution function, probability mass function, discrete probability distribution, an absolutely continuous univariate distribution, the like, any suitable distribution, or combinations thereof. In certain embodiments an allele frequency is provided as a relative value, fraction or percentage. In some embodiments an allele frequency is weighted and/or normalized. In certain embodiments an allele frequency is determine according to the presence, absence and/or frequency of an allele, haplotype or genotype in an individual or in at least 10, at least 500, at least 1000, at least 5000, at least 10,000 or at least 50,000 genomes. In certain embodiments a population allele frequency for one or more common polymorphisms is provided by, or obtained from data provided by, the International Genome Sample Resource (IGSR) (A global reference for human genetic variation (2015) Nature 526:68-74; An integrated map of structural variation in 2,504 human genomes (2015) Nature 52:75-81; [Online][Retrieved from the internet on Aug. 5, 2016 from <URL:http//www.1000genomes.org/data>]) or provided by the 1000 Genomes database ([Online][Retrieved from the internet on May 18, 2016, from <ftp-/ftp.1000genomes.ebi.ac.uk/vol1/ftp/release/20130502/LL.wgs.phase3_sha peit2_mvncall_integrated_v5b.20130502.sites.vcf.gzas>]).

In some embodiments an allele balance is determined for, and/or associated with, a given polymorphism of a subject's genome. In certain embodiments a method, process or system described herein comprises determining an allele balance for 1 or more common polymorphisms. In some embodiments, a method, process or system described herein comprises determining an allele balance for 1 to $10^7$, 1 to $10^6$, 1 to $10^5$, 1 to $10^4$, 1 to $10^3$ common polymorphisms. In some embodiments, a method, process or system described herein comprises determining an allele balance for at least 100,000, at least 200,000, at least 300,000, at least 400,000, at least 500,000, at least 600,000, at least 700,000, at least 800,000, at least 900,000, at least 1,000,000, at least 1,500,000 or at least 2,000,000 common polymorphisms in a genome. In certain embodiments, an allele balance is determined and/or calculated by comparing the counts of reads comprising sequence information for a particular common polymorphism which align to a reference sequence with 100 identity at the polymorphism site to the counts of reads which align to the same polymorphism site which contain an alternate allele sequence at the polymorphism site. In certain embodiments an allele balance may comprise an actual, average, median and/or normalized value or range, or the raw counts. In some embodiments an allele balance is normalized. In some embodiments an allele balance for a given common polymorphism in a genome of a subject is determined according to the formula below:

$$\text{Allele Balance}_i = n\_ref/(n\_ref + n\_alt)$$

where "n_ref" is the number of reads that align to a reference sequence at the site of polymorphism i, which reads include the polymorphism allele of the reference sequence (e.g., an exact match with the reference sequence at polymorphism t). The term "n_alt" is the number of reads that align to the reference sequence at the site of polymorphism i which include an alternative allele for polymorphism i and which reads do not match the reference sequence at polymorphism i. In many cases, the raw counts of n_ref and n_alt are used in place of the ratio described above.

In certain embodiments a method, process or system herein comprises determining an "absence of heterozygosity" (AOH) for one or more portions of a subject's genome. In certain embodiments a method, process or system herein comprises determining an AOH for one or more common polymorphism within a genome of a subject. In certain embodiments a method, process or system herein comprises determining an AOH for continuous stretches of a subject's genome. In certain embodiments a method, process or system herein comprises determining the presence of heterozygosity (e.g., normalcy, No AOH) for one or more common polymorphism within a genome of a subject. In certain embodiments a method, process or system herein comprises determining the presence of heterozygosity (e.g., normalcy, No AOH) for continuous stretches of a subject's genome. The presence or absence of heterozygosity for a given common polymorphism is often determined, in part, according to an allele balance for a given polymorphism. Accordingly, in certain embodiments, the presence or absence of heterozygosity for a given portion of a genome is determined according to a plurality of allele balance values for the portion of the genome. In some embodiments an AOH or no AOH determination (i.e., call) is generated according to a plurality of sequence reads comprising sequence information for a plurality of SNPs. In certain embodiments, an AOH or no AOH call is determined for a contiguous portion of a genome according to a plurality of reads obtained from the contiguous portion. In certain embodiments, an AOH or no AOH call is determined for a portion of a genome according to a plurality of allele balances determined for a plurality of common polymorphisms present within a contiguous portion of a subject's genome. An AOH and/or no AOH call, in certain embodiments, is determined according to, in part, a suitable statistical method, suitable probability function or suitable Bayesian probability function. In some embodiments, an AOH or no AOH call is determined by a process comprising a suitable statistical model, non-limiting examples of which include a maximum likelihood regression, a negative binomial statistical model of read counts, Expectation-Maximization (EM), Hidden Markov model (HMM), the like, or combinations thereof. In some embodiments, an AOH or no AOH call is determined by a process comprising a suitable Hidden Markov model (HMM). An HMM can comprise the use of one or more suitable algorithms non-limiting examples of which include a Viterbi algorithm, Forward algorithm, Baum-Welch algorithm, EM algorithm, the like, or combinations thereof.

In some embodiments an AOH score is determined. In some embodiments, an AOH or no AOH call is determined according to an AOH score that may fall within or outside a pre-defined threshold range of AOH scores. In some embodiments, AOH score represents that probability of the segment being in its called state, and is computed using the empirical likelihoods derived from a Hidden Markov model (HMM). In certain embodiments an AOH score is determined by the use of a suitable statistical method according to a predefined threshold and/or level of confidence. An AOH score can be derived from a suitable distribution function, probability function or density function.

In certain embodiments an absence of heterozygosity (AOH) for a portion of a genome is determined according to FIG. 11.

In some embodiments a system, process or method described herein determines the presence or absence of a copy number variation in a genome of one or more subjects. In certain embodiments a presence or absence of one or more copy number variations is determined for a portion of a genome of a subject or for an entire genome of a subject. In certain embodiments, a method, system or process herein can determine the presence or absence of 1, 2, 3, 4, 5, 6, 7, 8, 9, 10 or more, 20 or more, 50 or more, 500 or more or 1000 or more copy number variations in a genome. In some embodiments a copy number variation generally represents a particular genotype or haplotype present in a genome of a subject. In some embodiments a copy number variation is a portion of a genome that is duplicated or deleted. In some embodiments a copy number variation is a repeat, STR, deletion, or duplication within a chromosome or genome. In certain embodiments a copy number variation is a microduplication or microdeletion. A copy number variation can be of any length, and in some embodiments is about 50 base pairs (bp) to about 250 consecutive megabase pairs (Mbp) in length.

In certain embodiments a presence or absence of a copy number variation is determined, in part, according to the presence or absence of heterozygosity for a portion of a genome. For example, a contiguous portion of a genome that is determined to have an absence of heterozygosity, is sometimes determined as the presence of a copy number variation. In some embodiments the presence of heterozygosity for a portion of a genome is determined as the absence of a copy number variation. In some embodiments, relative read counts across the targeted regions is used to determined copy number variation or normalcy.

In some embodiments the presence or absence of heterozygosity, or presence or absence of a copy number variation can be determined for one or more portions of a genome. In some embodiments a portion of a genome is a contiguous portion of a subject's genome. In certain embodiments, a portion of a genome is a contiguous portion of a genome between about 10 bp and 250 Mb, between about 10 bp and about 100 Mb, or between about 250 bp and about 100 Mb in length. In some embodiments a portion of a genome is a contiguous portion of a subject's genome that is at least 50 bp in length, at least 100 bp in length, at least 150 bp in length, at least 200 bp in length, at least 250 bp in length, at least 300 bp in length, at least 400 bp in length, or at least 500 bp in length. The minimal length of a copy number variation that can be determined depends, in part, on the average, mean or absolute distance between 2 or more reads according to their mapped position within a genome or chromosome. For methods described herein, targeted primers can be designed to generate reads having an average, mean or absolute distance between reads of 50 to 50,000 base pairs, where each read provides sequence information for a common polymorphism. For portions of a genome where higher resolution is required, targeted primers can be designed to generate reads having a shorter average, mean or absolute distance between reads (e.g., between 50 to 1,000 base pairs). In certain embodiments, methods and processes described herein generate reads that are obtained from an entire genome where the average, mean or absolute distance between reads is between about 1000 bp and about 50,000 bp. In certain embodiments, methods and processes described herein generate reads that are obtained from an entire genome where the average, mean or absolute distance between reads is at least 1000 bp, at least 2000 bp, at least 4000 bp, at least 5000 bp, at least 6000 bp, at least 8000 bp, at least 10,000 bp, at least 12,000 bp, at least 15,000, at least 18,000 bp, or at least 20,000 bp. In certain embodiments, methods and processes described herein generate reads that are obtained from an entire genome where the average, mean or absolute distance between reads is at least 4000 bp, at least 5000 bp, at least 6000 bp, at least 8000 bp, or at least 10,000 bp.

In certain embodiments the presence of a copy number variation is associated with a medical condition. In certain embodiments the presence of a copy number variation is predictive of a medical condition or indicates a probability that a subject may develop a certain medical condition. Medical conditions associated with certain copy number variations are known.

Systems, Machines, Storage Mediums and Interfaces

Certain processes and methods described herein often cannot be performed without a computer, microprocessor, software, module or other machine. Methods described herein typically are, in part, or in full, computer-implemented methods. In certain embodiments one or more portions of a method are performed by one or more processors (e.g., microprocessors), computers, or microprocessor controlled machines. Embodiments pertaining to methods described in this document generally are applicable to the same or related processes implemented by instructions in systems, machines and computer program products described herein. Embodiments pertaining to methods described in this document generally can be applicable to the same or related processes implemented by a non-transitory computer-readable storage medium with an executable program stored thereon, where the program instructs a microprocessor to perform the method, or a part thereof. The descriptive term "non-transitory" as used herein is expressly limiting and excludes transitory, propagating signals (e.g., transmission signals, electronic transmissions, waves (e.g., carrier waves)). The terms "non-transitory computer-readable media" and/or "non-transitory computer-readable medium" as used herein comprise all computer-readable mediums except for transitory, propagating signals. In some embodiments, processes and methods described herein are performed by automated methods. In some embodiments one or more steps and a method described herein is carried out by a microprocessor and/or computer, and/or carried out in conjunction with memory. In some embodiments an automated method is embodied in software, modules, microprocessors, peripherals and/or a machine comprising the like, that (a) provide or obtain single-end sequence reads derived from an entire genome of a subject, wherein (i) the reads represent less than 5% of the entire genome, (ii) the average distance between the reads is at least 4000 bp, and (iii) the reads comprise sequence information for greater than 400,000 common polymorphisms, each read comprising the sequence information for at least one of the common polymorphisms; (b) determine a presence or absence of heterozygosity for each of the common polymorphisms according to the sequence information; and (c) determine the presence or absence of a copy number variation (CNV) for a portion of the genome according to the presence or absence of heterozygosity determined in (b).

Machines, software and interfaces may be used to conduct methods described herein. Using machines, software and interfaces, a user may enter, request, query or determine options for using particular information, programs or processes (e.g., obtaining reads, filtering reads, mapping reads, generating alignments, determining allele frequencies, determining allele balances, filtering data, applying statistical analysis, generating measures of statistical significance, calling AOH, and determining the presence or absence of a CNV, the like or a combination thereof), which can involve implementing statistical analysis algorithms, statistical significance algorithms, statistical error algorithms, statistical probability algorithms, iterative steps, validation algorithms, and graphical representations and outputs, for example. In some embodiments a data file may be entered by a user as input information, a user may download one or more data files by a suitable hardware media (e.g., flash drive), and/or a user may send a data set from one system to another for subsequent processing and/or providing a call or outcome (e.g., send sequence read data from a sequencer to a computer system for sequence read mapping; send mapped read data to a computer system for processing and yielding one or more allele balances, for example).

A system typically comprises one or more machines. Each machine comprises one or more of memory, one or more microprocessors, and instructions. Where a system includes two or more machines, some or all of the machines may be located at the same location, some or all of the machines may be located at different locations, all of the machines may be located at one location and/or all of the machines may be located at different locations.

A system sometimes comprises a computing apparatus or a sequencing apparatus, or a computing apparatus and a sequencing apparatus (i.e., sequencing machine and/or computing machine). Apparatus, as referred to herein, is sometimes a machine. A sequencing apparatus generally is configured to receive physical nucleic acid and generate signals corresponding to nucleotide bases of the nucleic acid. A sequencing apparatus is often "loaded" with a sample comprising nucleic acid and the nucleic acid of the sample loaded in the sequencing apparatus generally is subjected to a nucleic acid sequencing process. The term "loading a sequence apparatus" as used herein refers to contacting a portion of a sequencing apparatus (e.g., a flow cell) with a nucleic acid sample, which portion of the sequencing apparatus is configured to receive a sample for conducting a nucleic acid sequencing process. A sequencing apparatus is often configured, in part, to perform a suitable DNA sequencing method that generates signals (e.g., electronic signals, detector signals, data files, images, the like, or combinations thereof) corresponding to nucleotide bases of the loaded nucleic acid, thereby generating sequence reads.

Systems addressed herein may comprise general components of computer systems, such as, for example, network servers, laptop systems, desktop systems, handheld systems, personal digital assistants, cell phones systems, computing kiosks, and the like. A computer system may comprise one or more input means such as a keyboard, touch screen, mouse, voice recognition or other means to allow the user to enter data into the system. A system may further comprise one or more outputs, including, but not limited to, a display (e.g., CRT, LED or LCD), speaker, FAX machine, printer (e.g., laser, ink jet, impact, black and white or color printer), or other output useful for providing visual, auditory and/or hardcopy output of information (e.g., outcome and/or report).

In certain embodiments, data (e.g., sequence data) is generated by an in silico process, which data can be further analyzed and manipulated and subjected to methods and processes described herein. The term "in silico" refers to data and/or a manipulation or a transformation of data that is performed using a computer, one or more modules, or a combination thereof. In certain embodiments methods and processes herein are performed in silico.

A system may include software useful for performing a process described herein, and software can include one or more modules for performing such processes. The term "software" refers to computer-readable storage medium comprising program instructions (e.g., an executable program) that, when executed by a computer, perform computer operations. Instructions executable by the one or more microprocessors sometimes are provided as executable code, that when executed, can cause one or more microprocessors to implement a method described herein.

A module described herein can exist as software, and/or instructions (e.g., processes, routines, subroutines) embodied in the software which can be implemented or performed by a microprocessor. For example, a module can be a part of a program that performs a particular process or task. The term "module" refers to a self-contained functional unit that can be used in a larger machine or software system. A module can comprise a set of instructions for carrying out a function of the module by one or more microprocessors. Instructions of a module can be implemented in a computing environment by use of a suitable programming language, suitable software, and/or code written in a suitable language (e.g., a computer programming language known in the art) and/or operating system, non-limiting examples of which include UNIX, Linux, oracle, windows, Ubuntu, ActionScript, C, C++, C #, Haskell, Java, JavaScript, Objective-C, Perl, Python, Ruby, Smalltalk, SQL, Visual Basic, COBOL, Fortran, UML, HTML (e.g., with PHP), PGP, G, R, S, the like or combinations thereof.

In some embodiments a module comprises one or more data files and can transfer data files to another module and/or receive data files from another module. In some embodiments a module transforms data and/or information, for example, into tangible printed matter, instructions to a user, an alignment, an outcome, a display, a genotype, a karyotype plot, genomic CNV map, the like or combinations thereof. For example, one or more modules and/or microprocessors (e.g., apparatus or machines) described herein can generate optimal target sites, generate or obtain sequencing reads, map reads, generate, assemble, process and analyze sequencing information, generate allele balances, determine allele frequency, and determine the presence or absence of heterozygosity or CNVs within a genome. The process can be likened to a process of transforming millions of pieces of a puzzle into a picture or transforming bits of X-ray data into a display of a portion of a subject's body (e.g., a display of bones, organs, and other body tissues).

One or more modules can be utilized in a method described herein, non-limiting examples of which include a target site module, a sequencing module, a mapping module, a sequence information module, an allele frequency module, an allele balance module, an AOH Caller module, and CNV caller module, an outcome module, the like or combination thereof. Modules are sometimes controlled by a microprocessor. In certain embodiments a module or a machine comprising one or more modules, configured to gather, assemble, receive, obtain, access, process, analyze, recover, provide and/or transfer data and/or information to or from another module, machine, component, peripheral or user of a machine.

A module is sometimes embodied on a non-transitory computer-readable medium, and sometimes is tangibly embodied on a non-transitory computer-readable medium.

Modules and Computer Implementation

Figure 10:
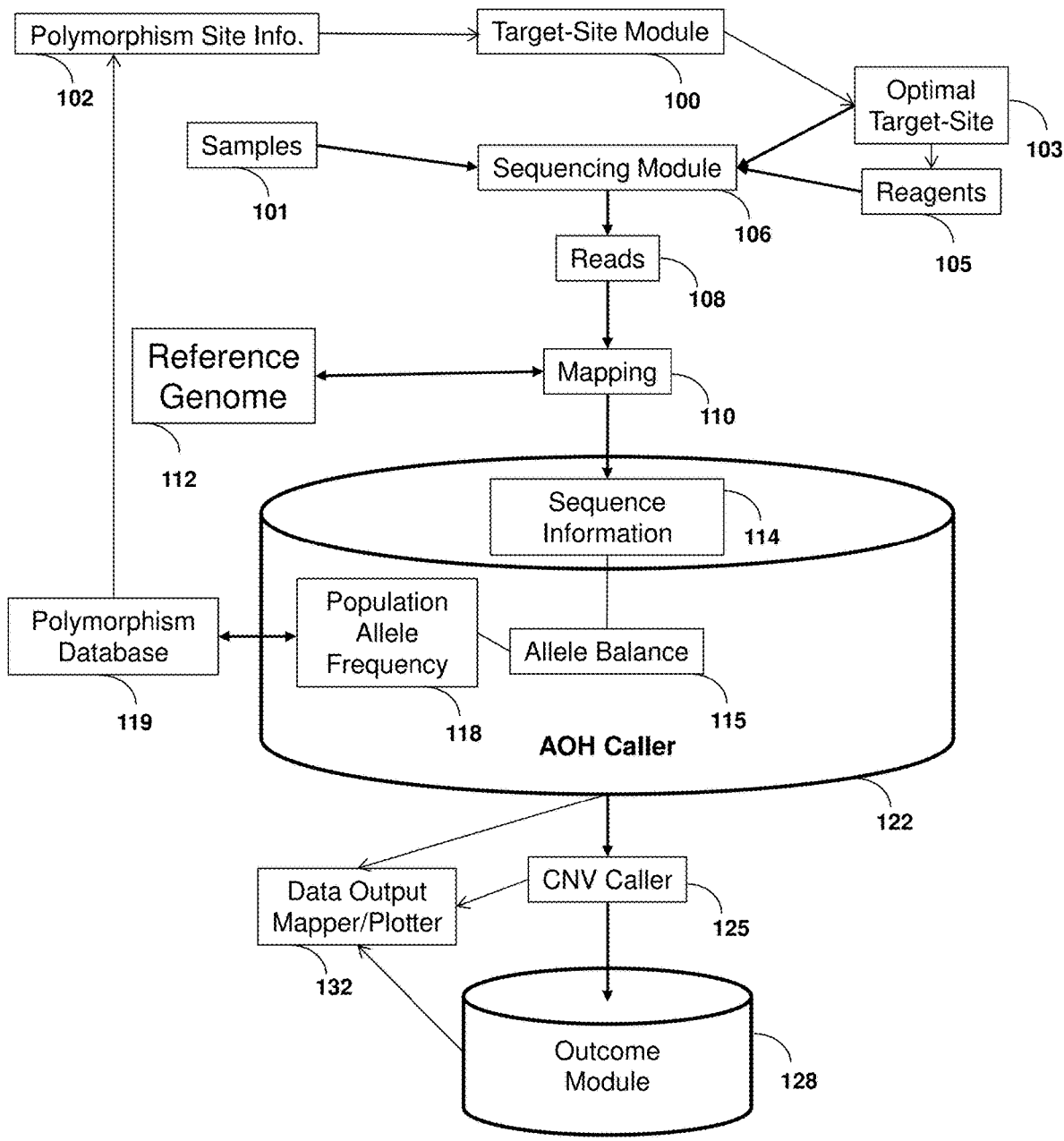
FIG. 10 shows a flow diagram illustrating an embodiment of a method, process and/or system described herein.

An example of a process and system presented herein is provided in FIG. 10. In some embodiments a system comprises a target-site module 100. In some embodiments a target-site module is configured to (i) analyze potential target sites for a plurality of characteristics, non-limiting examples of which include the presence of a common polymorphism, polymorphism sequence data, nearby nucleic acid sequences (e.g., within 1 to 400 bp of a polymorphism), sequence characteristics (e.g., GC content, melting temperature, variation rate, location, historical data, disease associations, the like and combinations thereof), distance between potential target-sites, the like and combinations thereof; and (ii) identify optimal loci for primer/probe binding, read generation and analysis. A target-site module 100 often receives data and/or information from user input and/or from one or more polymorphism databases 119 which provide polymorphisms information 102 including, but not limited to polymorphism sequence data, nearby nucleic acid sequence data, polymorphism genomic coordinates (loci), population data, allele frequency, disease associations, the like and combinations thereof. In some embodiments a target-site module identifies and provides optimal target-site information 103, which includes optimal polymorphism loci within a genome for primer design, primer binding and read generation (e.g., for generation of 100,000 to 2,000,000 reads, each providing sequence information for a different polymorphism). In some embodiments a target-site module provides a plurality of target-site primer sequences to be synthesized and delivered to a sequencing modules for generating reads. In certain embodiments a target-site module provides a plurality of target site scores for a plurality of polymorphisms within a genome which can be further analyzed and processed by a user or another module to provide optimal target site information. In certain embodiments a target-site module provides optimal target site information to a user or to a sequencing module.

In some embodiments a system comprises a sequencing module 106. In certain embodiments a sequencing module is configured to generate sequence reads 108, often by use of an NGS method. A sequence module may comprise a nucleic acid sequencer (e.g., a machine or apparatus designed and configured to generate sequence reads for a nucleic acid library) and/or software and instructions configured to generate, organize, associate and/or trim sequence reads. A nucleic acid sequencer often is configured to receive samples 101 (e.g., nucleic acids samples) and reagents 105, including primers and probes. A sequence module often provides sequence reads in the form of a data file (e.g., a bam file, a fasta file, and the like). A sequence module can provide sequence reads in any suitable file format. In certain embodiments sequence reads are transferred from a sequence module to a mapping module 110. In some embodiments a sequence module comprises a mapping module. In certain embodiments a sequencing module provides reads directly to an AOH caller module 122.

In some embodiments a system comprises a mapping module 110. In certain embodiments a mapping module receives reads from a sequence module. In some embodiments sequence reads are provided to a mapping module by a user and/or from a suitable data storage device. In certain embodiments reads are provided to a mapping module in the form of a storage medium. In some embodiments a mapping module is configured to map reads to a reference genome 112. In some embodiments a mapping module is configured to filter reads. In some embodiments a mapping module comprises a filter module which is configured to filter reads. In some embodiments a mapping module provides read quality scores. In certain embodiments a mapping module transfers data and/or sequence information 114 (e.g., mapped, filtered, processed and/or aligned reads) to an AOH caller module 122.

In some embodiments a system comprises an AOH caller 122. An AOH caller sometimes comprises population allele frequencies 118. In some embodiments an AOH caller determines or calculates allele frequencies and provide population allele frequencies 118. In certain embodiments an AOH caller can send and receive data from a polymorphism database 119, which can provide sequence data for common polymorphisms and/or population allele frequencies 118 for common polymorphisms to an AOH caller module. In certain embodiments an AOH caller receives sequence information from a sequencing module or mapping module, and calculates allele frequencies. In certain embodiments an AOH caller receives sequence information from a sequencing module or mapping module, and calculates allele balances for a plurality of common polymorphisms. In some embodiments an AOH caller determines the presence or absence of heterozygosity for a plurality of loci within a subject's genome. In some embodiments an AOH caller determines the presence or absence of heterozygosity for a plurality of loci within a subject's genome and sends AOH or no AOH calls to a CNV caller module 125 or to a data output module 132. A data output module 132 can send and receive data and/or information (e.g., AOH calls, CNV calls and/or outcomes) to and from an AOH caller, CNV caller and an outcome module 128 and provide data and/or information to a user, another module or to a peripheral, such as a display (e.g., an interactive display) or a printer.

In some embodiments a system comprises an outcome module 128. In certain embodiments an outcome module receives data and/or information (e.g., data files) from an AOH caller or CNV caller module. In certain embodiments an outcome module determines an outcome. Often an outcome is provided by an outcome module. An outcome sometimes is provided to a health care professional (e.g., laboratory technician or manager; physician or assistant) from an outcome module. An outcome module may comprise a suitable mathematical and/or statistical software package. In certain embodiments an outcome module comprises a data output module which generates a plot, table, chart or graph. In some embodiments an outcome module generates and/or compares standard statistical scores. The presence or absence of a CNV and/or associated medical condition (e.g., an outcome) is often determined by and/or provided by an outcome module. The likelihood of the presence or absence of a CNV and/or associated medical condition (e.g., an outcome) is often determined by and/or provided by an outcome module. In certain embodiments the absence of a CNV (e.g., in a gene of interest) is determined by an outcome module. An outcome module can be specialized for determining the presence or absence of a specific CNV that is associated with a medical condition, or a likelihood that a subject will develop a medical condition. In some embodiments an outcome module assemble a representation of a subject's genome, including a representation of the presence or absence of heterozygosity and one or more CNVs for some or all portions of the subject's genome.

EXAMPLES

The examples set forth below illustrate certain embodiments and do not limit the technology.

Example 1

A diagnostic test for detection of cytogenomic copy number variation and absence of heterozygosity in which samples from blood, saliva or other sample types are processed through next generation sequencing.

Example 2: Examples of Embodiments

A1. A method of genome analysis comprising:
a) generating single-end sequence reads obtained from an entire genome of a subject, wherein (i) the reads represent less than 5% of the entire genome, (ii) the average distance between any two of the reads is at least 4000 bp, and (iii) the reads comprise sequence information for greater than 400,000 common polymorphisms, each read comprising the sequence information for at least one of the common polymorphisms; and
b) determining the presence or absence of a copy number variation (CNV) for a portion of the genome.

A2. The method of embodiment A1, wherein an average distance between any two of the greater than 400,00 common polymorphisms at least 4000 bp.

A3. The method of embodiment A1 or A2, wherein each read comprises the sequence information for a different common polymorphisms.

A4. The method of any one of embodiments A1 to A3, wherein prior to b), a presence or absence of heterozygosity is determined for each of the common polymorphisms according to the sequence information, and the presence of absence of a copy number is determined for the portion of the genome according to the presence or absence of heterozygosity determined.

A5. The method of any one of embodiments A1 to A3, wherein prior to b), an allele balance is determined for each of the common polymorphisms according to the sequence information, and the presence of absence of a copy number is determined for the portion of the genome according to the allele balances determined for each of the polymorphisms.

B1. A method of genome analysis comprising:
 a) generating single-end sequence reads obtained from an entire genome of a subject, wherein (i) the reads represent less than 5% of the entire genome, (ii) the reads comprise sequence information for greater than 400,000 target sites within the entire genome, (iii) each target site comprises a different common polymorphism, and (iv) the average distance between the any two target sites within the genome is at least 4000 bp, and (v), and each of the reads comprises the sequence information for one of the common polymorphisms; and
 b) determining the presence or absence of a copy number variation (CNV) for a portion of the genome.

B2. The method of embodiment B1, wherein prior to b), a presence or absence of heterozygosity is determined for each of the different common polymorphisms according to the sequence information, and the presence of absence of a copy number is determined for the portion of the genome according to the presence or absence of heterozygosity.

B3. The method of embodiment B1, wherein prior to b), an allele balance is determined for each of the common polymorphisms according to the sequence information, and the presence of absence of a copy number is determined for the portion of the genome according to the allele balances determined for each of the polymorphisms.

C1. A method of genome analysis comprising:
 a) generating single-end sequence reads obtained from an entire genome of a subject, wherein (i) the reads represent less than 5% of the entire genome, (ii) the average distance between the reads is at least 4000 bp, and (iii) the reads comprise sequence information for greater than 400,000 common polymorphisms, each read comprising the sequence information for at least one of the common polymorphisms;
 b) determining a presence or absence of heterozygosity for each of the common polymorphisms according to the sequence information; and
 c) determining the presence or absence of a copy number variation (CNV) for a portion of the genome according to the presence or absence of heterozygosity determined in (b).

C2. The method of embodiment C1, wherein the presence or absence of a copy number variation is determined by a process comprising a Hidden Markov Model or Viterbi algorithm statistical model.

C3. The method of embodiments C1 or C2, wherein the presence or absence of a copy number variation is determined by a process comprising maximum likelihood regression, a negative binomial statistical model of the read-counts, or Expectation-Maximization.

C4. The method of any one of embodiments C1 to C3, wherein the method further comprises, prior to (b), determining an allele balance for one or more of the greater than 400,000 common polymorphisms.

C5. The method of embodiment C4, wherein the presence or absence of heterozygosity is determined according to the allele balance determined for the one or more of the greater than 400,000 common polymorphisms.

C6. The method of any one of embodiments C1 to C5, wherein the sequence information comprises a haplotype for an allele of the subject's genome for a common polymorphism.

C7. The method of any one of embodiments C1 to C6, wherein the presence or absence of heterozygosity for each polymorphism is determined by a process comprising a probability function.

C8. The method of any one of embodiments C1 to C7, wherein the presence or absence of a copy number variation (CNV) for a portion of the genome is determined according to the presence or absence of heterozygosity determined for a plurality of the polymorphisms located within the portion of the genome.

C9. The method of any one of embodiments C1 to C8, wherein the absence of heterozygosity for each of the common polymorphisms is determined in (b).

C10. The method of any one of embodiments C1 to C9, wherein the presence of a copy number variation (CNV) for a portion of the genome is determined in (c) according to the absence of heterozygosity determined in (b) for the portion of the genome.

C11. The method of any one of embodiments C1 to C10, wherein the portion of the genome is at least 100 kbp.

C12. The method of any one of embodiments C1 to C11, wherein the presence or absence of a CNV is determined for a portion of the genome that is 50 to 250 kbp.

C13. The method of any one of embodiments C1 to C12, wherein the presence or absence of a CNV is determined for a portion of the genome that is at least 250 kbp.

C14. The method of any one of embodiments C1 to C13, wherein the subject is a human.

C15. The method of any one of embodiments C1 to C14, wherein the sequence information of the reads comprises at least 1% of a nucleic acid of each chromosome in the genome of the subject.

C16. The method of any one of embodiments C1 to C15, wherein the single-end reads are generated in a single sequencing run or from a single flow cell.

C17. The method of any one of embodiments C1 to C16, wherein the reads are generated from at least 400,000 different targeted primers.

C18. The method of any one of embodiments C1 to C17, wherein each of the reads are between about 50 and about 200 nucleotides in length.

C19. The method of any one of embodiments C1 to C18, wherein the method does not comprise generating paired-end reads.

C20. The method of any one of embodiments C1 to C19, wherein the reads are obtained by an next generation sequencing (NGS) method.

C21. The method of any one of embodiments C1 to C20, wherein the sequence information comprises a nucleic acid sequence of one or more intron/exon junctions.

C22. The method of any one of embodiments C1 to C21, wherein the method comprises generating at least 400,000 non-overlapping, single-end sequence reads.

C23. The method of any one of embodiments C1 to C22, wherein the average distance between reads is at least 5000 bp.

C24. The method of any one of embodiments C1 to C23, wherein the reads represent less than 2% of the nucleic acid sequence of the entire genome of the subject.

C25. The method of any one of embodiments C1 to C24, wherein the determining of (b), or the determining of (c) is performed in silico using at least one processor and memory.

C26. The method of any one of embodiments C1 to C25, wherein the presence or absence of heterozygosity is determined using a Hidden Markov Model or Viterbi algorithm statistical model.

C27. The method of any one of embodiments C1 to C26, wherein the presence or absence of heterozygosity is determined using a maximum likelihood regression, a negative binomial statistical model of the read-counts, or Expectation-Maximization.

C28. The method of any one of embodiments C1 to C27, wherein determining the presence or absence of a CNV comprises determining an absence of heterozygosity (AOH) score for a plurality of polymorphisms within the portion of the genome.

C29. The method of embodiment C28, wherein the AOH score for each polymorphism is weighted according to a genomic distance between two or more reads within the portion of the genome.

C30. The method of any one of embodiments C1 to C29, wherein the greater than 400,000 common polymorphisms are distributed across the entire genome.

C31. The method of any one of embodiments C1 to C30, wherein each of the greater than 400,000 common polymorphisms are different polymorphisms.

C32. The method of any one of embodiments C1 to C31, wherein the common polymorphisms comprise single nucleotide polymorphisms (SNPs).

C33. The method of any one of embodiments C1 to C32, wherein an AOH score is determined for substantially all of the common polymorphisms.

C34. The method of any one of embodiments C1 to C33, wherein the presence of a copy number variation indicates the presence of a genetic disorder or medical condition.

C35. The method of any one of embodiments C1 to C34, wherein the method comprises, prior to (a), determining the optimum loci within the genome to generate the sequence reads, wherein the optimal loci are determined according to a target-site scoring process.

C36. The method of embodiment C35, wherein the target-site scoring process comprises generating a target score for a plurality of common polymorphisms and identifying optimum loci using a probability function or a distribution function.

C37. The method of embodiments C35 or C36, wherein the target-site scoring process comprises determining a percent GC content for a plurality of potential target sites.

C38. The method of any one of embodiments C1 to C37, wherein the target-site scoring process comprises determining a melting temperature for one or more potential target primers.

C39. The method of any one of embodiments C1 to C38, wherein the reads are non-overlapping reads.

C40. A computer implemented system for performing a genome analysis comprising:
  a) providing or obtaining non-overlapping, single-end sequence reads obtained from an entire genome of a subject, wherein (i) the reads represent less than 5% of the entire genome, (ii) the average distance between reads is at least 4000 bp, and (iii) the reads comprise sequence information for greater than 400,000 common polymorphisms, each read comprising the sequence information for at least one of the common polymorphisms;
  b) determining a presence or absence of heterozygosity for each of the common polymorphisms according to the sequence information; and
  c) determining the presence or absence of a copy number variation (CNV) for a portion of the genome according to the presence or absence of heterozygosity determined in (b).

C41. A non-transitory computer-readable storage medium comprising an executable program stored thereon, wherein the program instructs a microprocessor to:
  a) determine a presence or absence of heterozygosity (AOH) for plurality of common polymorphisms of a genome of a subject according to sequence information obtained from (i) single-end sequence reads obtained from an entire genome of the subject, wherein (ii) the reads represent less than 5% of the entire genome, (ii) the average distance between any two reads is at least 4000 bp, (iii) the reads comprise sequence information for greater than 400,000 common polymorphisms, and (iv) each read comprises the sequence information for at least one of the greater than 400,000 common polymorphisms; and
  b) determine the presence or absence of a copy number variation for a portion of the genome according to the AOH determined in (a).

The examples set forth above illustrate certain embodiments and do not limit the technology.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents.

Modifications may be made to the foregoing without departing from the basic aspects of the technology. Although the technology has been described in substantial detail with reference to one or more specific embodiments, those of ordinary skill in the art will recognize that changes may be made to the embodiments specifically disclosed in this application, yet these modifications and improvements are within the scope and spirit of the technology.

The technology illustratively described herein suitably may be practiced in the absence of any element(s) not specifically disclosed herein. Thus, for example, in each instance herein any of the terms "comprising," "consisting essentially of," and "consisting of" may be replaced with either of the other two terms. The terms and expressions which have been employed are used as terms of description and not of limitation, and use of such terms and expressions do not exclude any equivalents of the features shown and described or portions thereof, and various modifications are possible within the scope of the technology claimed. The term "a" or "an" can refer to one of or a plurality of the elements it modifies (e.g., "a reagent" can mean one or more reagents) unless it is contextually clear either one of the elements or more than one of the elements is described. The term "about" as used herein refers to a value within 10% of the underlying parameter (i.e., plus or minus 10%), and use of the term "about" at the beginning of a string of values modifies each of the values (i.e., "about 1, 2 and 3" refers to about 1, about 2 and about 3). For example, a weight of "about 100 grams" can include weights between 90 grams and 110 grams. Further, when a listing of values is described herein (e.g., about 50%, 60%, 70%, 80%, 85% or 86%) the listing includes all intermediate and fractional values thereof (e.g., 54%, 85.4%). Thus, it should be understood that although the present technology has been specifically disclosed by representative embodiments and optional features, modification and variation of the concepts herein disclosed may be resorted to by those skilled in the art, and such modifications and variations are considered within the scope of this technology.

Certain embodiments of the technology are set forth in the claim(s) that follow(s).

What is claimed is:

1. A computer implemented system for performing a genome analysis comprising:
   a) providing single-end sequence reads that represent less than 5% of the entire genome of a subject, wherein (i) the average distance between reads is at least 4000 bp, (ii) the reads comprise sequence information for greater than 400,000 polymorphisms, and (iii) each read comprises sequence information for at least one of the polymorphisms;
   b) determining a presence or absence of heterozygosity for each of the polymorphisms according to the sequence information; and
   c) determining the presence or absence of a copy number variation (CNV) for a portion of the genome according to the presence or absence of heterozygosity determined in (b).

2. The method of claim 1, wherein the presence or absence of the copy number variation is determined by a process comprising a Hidden Markov Model or Viterbi algorithm statistical model, maximum likelihood regression, a negative binomial statistical model of the read-counts, or Expectation-Maximization.

3. The method of claim 1, wherein the method further comprises, prior to (b), determining an allele balance for one or more of the greater than 400,000 polymorphisms, and optionally determining the presence or absence of heterozygosity according to the allele balance.

4. The method of claim 1, wherein the sequence information comprises a haplotype for an allele of the subject's genome for one or more of the polymorphisms.

5. The method of claim 1, wherein the presence or absence of heterozygosity is determined by a process comprising a probability function.

6. The method of claim 1, wherein the absence of heterozygosity for each of the polymorphisms is determined in (b).

7. The method of claim 1, wherein the presence of the copy number variation (CNV) for a portion of the genome is determined in (c) according to the absence of heterozygosity determined in (b) for the portion of the genome.

8. The method of claim 7, wherein the portion of the genome is at least 100 kbp.

9. The method of claim 8, wherein the sequence information of the reads comprises at least 1% of a nucleic acid sequence of each chromosome in the genome of the subject.

10. The method of claim 1, wherein the single-end reads provided were, prior to (a), obtained by a process comprising a next generation sequencing (NGS) method, and were generated in a single sequencing run or from a single flow cell.

11. The method of claim 1, wherein the reads provided are non-overlapping reads and, prior to (a), were generated from at least 400,000 different targeted primers.

12. The method of claim 1, wherein each of the reads are between about 50 and about 200 nucleotides in length.

13. The method of claim 1, wherein the method does not comprise generating paired-end reads.

14. The method of claim 1, wherein the sequence information comprises a nucleic acid sequence of one or more intron/exon junctions.

15. The method of claim 1, wherein the determining of the presence or absence of a CNV comprises determining an absence of heterozygosity (AOH) score for a plurality of the greater than 400,000 polymorphisms, where the AOH score for each polymorphism is weighted according to a genomic distance between two or more the reads within the portion of the genome.

16. The method of claim 15, wherein the AOH score is determined for substantially all of the polymorphisms.

17. The method of claim 1, wherein one or more, or all of the greater than 400,000 polymorphisms comprise single nucleotide polymorphisms (SNPs).

18. The method of claim 1, wherein the presence of the copy number variation indicates the presence of a genetic disorder or medical condition.

19. The method of claim 1, wherein the subject is a human.

20. A non-transitory computer-readable storage medium comprising an executable program stored thereon, wherein the program instructs a microprocessor to:
   a) obtain a plurality of single-end sequence reads that represent less than 5% of the entire genome of a subject, wherein (i) the average distance between reads is at least 4000 bp, (ii) the reads comprise sequence information for greater than 400,000 polymorphisms, and (iii) each read comprises sequence information for at least one of the polymorphisms;
   b) determine a presence or absence of heterozygosity for each of the polymorphisms according to the sequence information; and
   c) determine the presence or absence of a copy number variation (CNV) for a portion of the genome according to the presence or absence of heterozygosity determined in (b).

* * * * *